United States Patent
Rong et al.

(10) Patent No.: US 9,676,789 B2
(45) Date of Patent: Jun. 13, 2017

(54) AMINATED DERIVATIVE OF HOMOHARRINGTONINE, PREPARATION METHOD THEREFOR, AND APPLICATION THEREOF

(75) Inventors: Frank Rong, Zhejiang (CN); Rongzhen Xu, Zhejiang (CN); Fuwen Xie, Fujian (CN); Hongxi Lai, Fujian (CN)

(73) Assignee: HANGZHOU BENSHENG PHARMACEUTICAL CO., LTD., Zhhejiang (CN)

( * ) Notice: Subject to any disclaimer, the term of this patent is extended or adjusted under 35 U.S.C. 154(b) by 477 days.

(21) Appl. No.: 14/239,464

(22) PCT Filed: Aug. 20, 2012

(86) PCT No.: PCT/CN2012/080349
§ 371 (c)(1),
(2), (4) Date: Mar. 28, 2014

(87) PCT Pub. No.: WO2013/023620
PCT Pub. Date: Feb. 21, 2013

(65) Prior Publication Data
US 2014/0206669 A1    Jul. 24, 2014

(30) Foreign Application Priority Data

Aug. 18, 2011 (WO) ............... PCT/CN2011/078586

(51) Int. Cl.
*C07D 493/16* (2006.01)
*C07D 491/20* (2006.01)

(52) U.S. Cl.
CPC ......... *C07D 493/16* (2013.01); *C07D 491/20* (2013.01)

(58) Field of Classification Search
None
See application file for complete search history.

(56) References Cited

U.S. PATENT DOCUMENTS

2005/0090484 A1    4/2005    Robin et al.

FOREIGN PATENT DOCUMENTS

| CN | 1660848 A | 8/2005 |
| WO | 02/32904 A1 | 4/2002 |
| WO | 02074314 A1 | 9/2002 |
| WO | 2009148654 A2 | 12/2009 |

OTHER PUBLICATIONS

Takeda et al., Antitumor Activities of Harringtonine and Homoharringtonine, Cephalotaxus Alkaloids which are Active Principles from Plant by Intraperitoneal and Oral Administration, 1982, J.Pharm.Dyn., 5, pp. 841-847.*

Morita et al. (2000) "Cephalezomines A-F, Potent Cytotoxic Alkaloids from *Cephalotaxus harringtonia* var. *nana*," Tetrahedron. 56(19):2929-2934.

Powell et al. (1972) "Antitumor alkaloids from Cephalotaxus harringtonia: Structure and activity," Journal of Pharmaceutical Sciences. 61(8):1227-1230.

International Search Report with Written Opinion corresponding to International Patent Application No. PCT/CN2012/080349, mailed Nov. 29, 2012.

Supplementary European Search Report corresponding to European Patent Application No. 12823351.7, dated Dec. 4, 2014.

* cited by examiner

*Primary Examiner* — Kortney L Klinkel
*Assistant Examiner* — Tori M Strong
(74) *Attorney, Agent, or Firm* — Lathrop & Gage LLP; Brian C. Trinque

(57) ABSTRACT

The present invention belongs to the field of natural medicine and pharmaceutical chemistry and specifically relates to novel aminated homoharringtonine derivatives of formula (I) and a pharmaceutically acceptable salt thereof, to a process for the preparation of these compounds, compositions containing such compounds and their use in preparing antineoplastic medicaments.

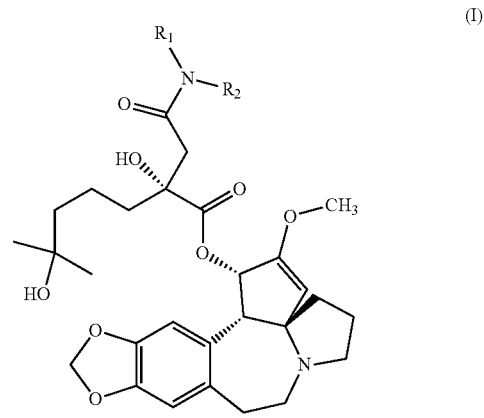

6 Claims, No Drawings

AMINATED DERIVATIVE OF HOMOHARRINGTONINE, PREPARATION METHOD THEREFOR, AND APPLICATION THEREOF

RELATED APPLICATIONS

This application is a 35 U.S.C. §371 filing of International Application No. PCT/CN2012/080349, filed Aug. 20, 2012; which claims priority to International Patent Application No. PCT/CN2011/078586, filed Aug. 18, 2011. The entire contents of each are incorporated herein by reference.

TECHNICAL FIELD

The present invention belongs to the field of natural medicine and pharmaceutical chemistry, and relates to novel homoharringtonine derivatives, in particular aminated homoharringtonine derivatives, to a process for the preparation of these compounds, compositions containing such compounds and their use in preparing antineoplastic medicaments.

BACKGROUND OF THE INVENTION

Homoharringtonine (HHT), also known as O-3-[(2R)-2,6-dihydroxy-2-(2'-methoxy-2'-oxoethyl)-6-methylheptanoyl]cephalotaxine, is an alkaloid extracted and separated from Chinese herbal plants of Cephalotaxaceae family, in particular from *cephatotaxus fortuneif* or congeners thereof. *Cephatotaxus* genus plants of the Cephalotaxaceae family consist of 9 species, 8 of which are originated in China. Plants of this genus contain a plurality of alkaloids, in which harringtonine, homoharringtonine, isoharringtonine and deoxyharringtonine have been extracted, identified and extensively investigated [ZHONG Sanbao et al., Studies on Semi-synthesis of Cephalotaxine Esters and Correlation of Their Structures with Antitumor activity, *Acta Pharmaceutica Sinica*, 1994, 29 (1), 33-39; WANG Dingzhi et al., Studies on Alkaloids in *Cephatotaxus* genus Plants, *Acta Pharmaceutica Sinica*, 1992, 03, 178-184]. Furthermore, a non-ester alkaloid (i.e. cephalotaxine) is also separated from *Cephatotaxus* as a main component.

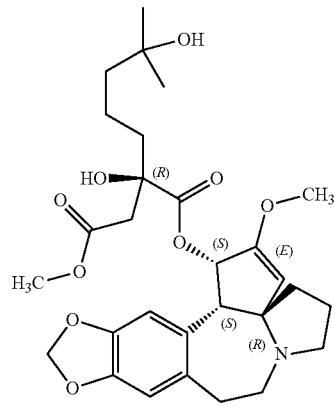

Homoharringtonine
CAS: 26833-87-4

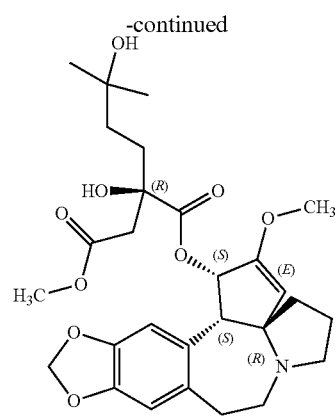

Harringtonine
CAS: 26833-85-2

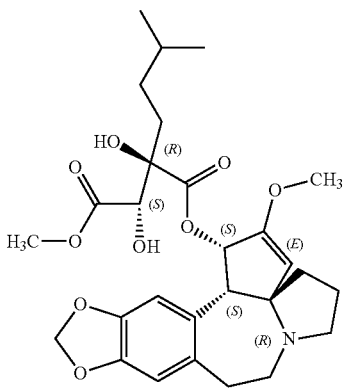

Isoharringtonine
CAS: 26833-86-3

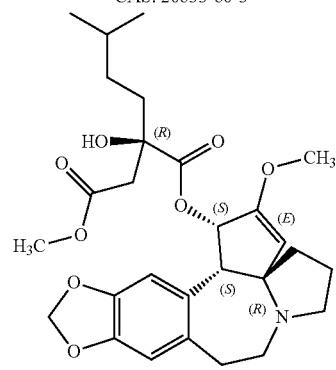

Deoxyharringtonine
CAS: 36804-95-2

Clinical studies demonstrate that HHT can be applied in the remission induction and post-remission treatment of acute myeloid leukemia, in the treatment of myelodysplastic syndrome (MDS), chronic myelogenous leukemia, polycythemia vera and malignant lymphoma, etc., particularly in the treatment of acute non-lymphocytic leukemia [ZHANG, Zhixue et al., Clinical study of HAG projects for the treatment of middle and high risk myeloid hyperplasia singular syndrome and acute myeloid leukemia, *Journal of Jinggangshan University*, 2010, 31(6),108-110; DENG, Jianqun et al., The impact of homoharringtonine to leukemia proto-oncogene bcl-2, c-myc, tumor suppressor gene p15, *Chin J of Clinical Rational Drug Use*, 2010, 3(7), 15-16; CHEN, Lijuan et al., A Study of Apoptosis on Non-lymphocytic Leukemia Cells Induced by Cytosine Arabinoside and Homoharringtonine, *Jiangsu Medical Journal*, 1999, 25(4), 257-258; ZHANG, Hui et al., 27 clinical analysis of LD-HA regimen in the treatment of acute myeloid leukemia, *Acta Academiae Medicinae Suzhou*, 1997, 17(4), 689-690; DING, Suxin et al., 26 clinical analysis of LD-HA regimen in the treatment of hypoplastic leukemia, *Acta Academiae Medicinae Suzhou*, 1997, 17(1), 89-90; XUE, Yanping et al., Clinical observation of HAD regimen in the treatment of adult acute non-lymphocytic leukemia, *Chinese Journal of Hematology*, 1995, 16(2), 59-61].

HHT can promote cell differentiation and apoptosis [WANG Yun et al., Experimental study of K562 and CML cell apoptosis and differentiation induced by homoharringtonine, *Shanghai Medical Journal*, 2001, 24(3), 166-168; LU, Dayong et al., Effect of homoharringtonine on leukemia cell differentiation and tumor metastasis, *Journal of Shanghai University*, 1999, 5(2), 175-177].

According to the studies on the synchronous KB (human oral epidermoid carcinoma) cells, HHT possesses cell cycle specificity and has the strongest killing effect on the cells in G1 and G2 phases and a relatively weaker effect on cells in S phase [JIN, Wei et al., Studies on the effect of homoharringtonine on HL-60 cells and QCY7703 cells, *Acta Chinese Medicine and Pharmacology*, 2001, 29(3), 44-45; LUO, Chenmei et al., Effect of homoharringtonine and Xueshuantong on human pterygium fibroblasts cell cyclic variation, *Journal of Traditional Chinese Ophthalmology*, 1999, 9(2), 67-70].

The pharmacological effects of HHT are mainly in inhibiting the protein synthesis of the eukaryotic cells, inhibiting the binding of aminoacyl-tRNA to riboses and the formation of the ribosomes thereof and peptide chains, thereby affecting the early stages of polymer formation, and causing the polyribosomes to disaggregate, interfering ribosomal protein functions, and also inhibiting the synthesis of intracellular DNAs [CAI, Zhen et al., Involvement of apoptosis-related gene Survivin, bcl-2 and bax in the homoharringtonine-induced apoptosis of myelodysplastic syndrome cell line(MUTZ-1), *Journal of Practical Oncology*, 2003, 18(3), 188-191; CAI, Zhen et al., Expression of survivin mRNA in HHT-induced cell apoptosis of hematological malignancy cell lines, *Journal of Zhejiang University*, 2006, 35(2), 204-208; WANG, Hengxiang et al., Homoharringtonine Induces Apoptosis of K562 Cells through Inhibition of P210bcr/abl, *Chinese Journal of Experimental Hematology*, 2000, 8(4), 287-289; CHEN, Chunyan et al., Comparative proteomics research of apoptosis initiation induced by homoharringtonine in HL-60 cells, *Chinese Journal of Hematology*, 2003, 24(12), 624-628; LI, Yufeng et al., Effect of homoharringtonine on the telomerase activity of bone marrow CD34+ cells in patients of chronic myeloid leukemia, *Journal of Leukemia-Lymphoma*, 2004, 13(1), 42-43; LI, Yufeng et al., Effect of homoharringtonine on bone marrow CD34$^-$+CD7$^-$+cells in patients of chronic myeloid leukemia, *Chinese Journal of Hematology*, 2007, 28(10), 706-707; LI, Yufeng et al., Effect of homoharringtonine on T and Th lymphocytes subsets in patients of chronic myeloid leukemia, *Leukemia-Lymphoma*, 2006, 15(1), 37-39; LI, Yufeng et al., Effect of homoharringtonine on the telomerase activity of bone marrow cells and K562 cells in patients of chronic myeloid leukemia, *Chinese Journal of Hematology*, 2003, 24(6), 329-329; MENG, Xiaoli, Effects of homoharringtonine on telomerase activity in HL60 cells, *Journal of Zhengzhou University*, 2004, 39(3), 440-442; XIE, Wanzhuo et al., Effect of telomerase in homoharringtonine-induced apoptosis of HL-60 cells, *Chinese Journal of Medical Genetics*, 2002, 19(2), 169-171].

On the other hand, aminated or amidated small molecules have been widely applied in pharmaceutical research, development and applications. However, reports on the synthesis and application of aminated or amidated homoharringtonine derivatives have not yet been seen.

SUMMARY OF THE INVENTION

One object of the present invention is to provide novel aminated or amidated homoharringtonine derivatives characterized by formula (I)

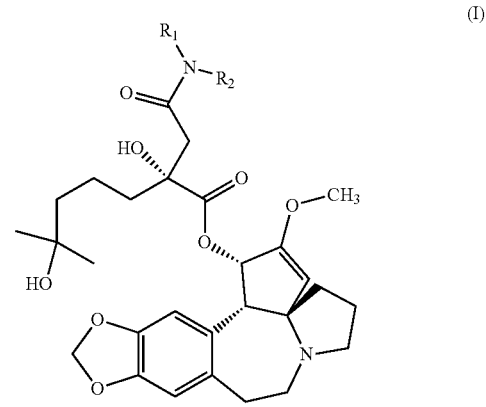

wherein $R_1$ and $R_2$ are selected from H, substituted or unsubstituted $C_1$-$C_{18}$ alkyl, substituted or unsubstituted $C_2$-$C_{18}$ alkenyl or alkynyl, substituted or unsubstituted $C_3$-$C_7$ cycloalkyl or alkenyl, substituted or unsubstituted aryl, substituted or unsubstituted heterocyclyl or heteroaryl. The substituent is selected from the group consisting of halogen, amino, $C_1$-$C_6$ substituted amino, nitro, cyano, hydroxyl, $C_1$-$C_6$ alkoxy, thiol and $C_1$-$C_6$ alkylthio. $R_1$ and $R_2$ can be identical or different, or together with the nitrogen atom to which they are attached form a ring, or a pharmaceutically acceptable adduct, complex or salt thereof.

Another object of the present invention is to provide a process for preparing the aminated or amidated homoharringtonine derivatives of formula (I) of the present invention:

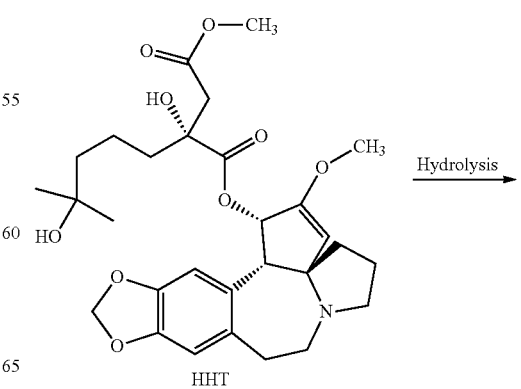

HHT

-continued

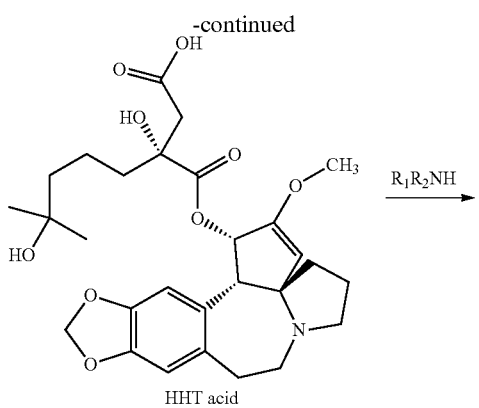
HHT acid $R_1R_2NH \longrightarrow$

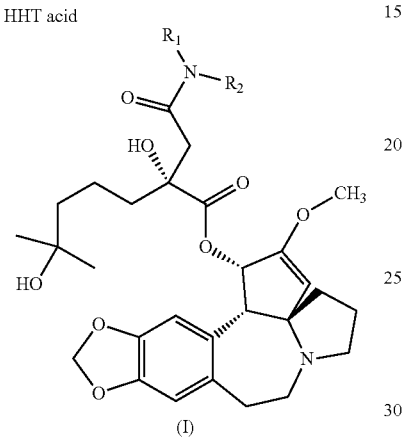
(I)

The aminated or amidated homoharringtonine derivatives of formula (I) of the present invention can be prepared in a two-step reaction as shown in the above scheme. Firstly, subject homoharringtonine to mild hydrolysis in the presence of an alkali or an alkaline reagent to produce an acid homoharringtonine as an intermediate, and then subject said intermediate and an appropriate organic amine $R_1R_2NH$ to condensation amination in the presence of a condensation agent and an alkali to produce an aminated or amidated homoharringtonine derivative. Alternatively, subject homoharringtonine and an appropriate organic amine $R_1R_2NH$ to a one-step condensation amination in the presence of a condensation agent or an alkaline reagent and produce an aminated or amidated homoharringtonine derivative. $R_1$ and $R_2$ in formula (I) are as defined above for formula (I).

Another object of the present invention is to provide a pharmaceutical composition containing the compounds of the present invention, wherein said pharmaceutical composition comprises at least one compound of the present invention and optionally a pharmaceutically acceptable excipient.

Yet another object of the present invention is to provide use of the compound of the present invention or the pharmaceutical composition comprising said compound in the manufacture of a medicament, in particular an antitumor medicament. Accordingly, the present invention also provides a method for treating a subject suffering from tumor, comprising administering to the subject in need thereof an effective amount of at least one compound of the present invention. Said tumor is particularly selected from leukemia, multiple myeloma, lymphoma, liver cancer, gastric cancer, breast cancer, cholangiocellular carcinoma, pancreatic cancer, lung cancer, colorectal cancer, osteosarcoma, melanoma, human cervical cancer, glioma, nasopharyngeal carcinoma, laryngeal carcinoma, esophageal cancer, middle ear tumor and prostate cancer, etc.

The present invention also relates to the compounds of the present invention used for treating a tumor.

DETAILED DESCRIPTION OF THE INVENTION

Specifically, the present invention relates to the following items in particular.
1. An aminated homoharringtonine derivative of formula (I) wherein

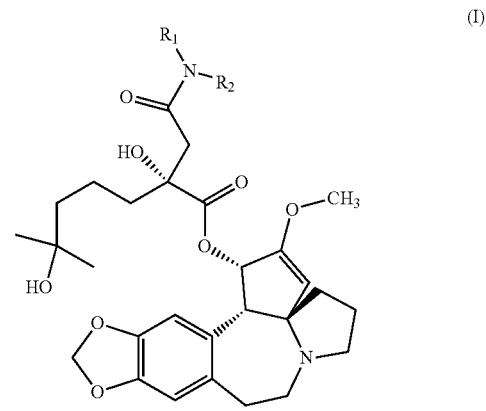
(I)

$R_1$ and $R_2$ are independently selected from H, $C_1$-$C_{18}$ alkyl, $C_2$-$C_{18}$ alkenyl, $C_2$-$C_{18}$ alkynyl, $C_3$-$C_7$ cycloalkyl or cycloalkenyl, aryl, heterocyclyl, heteroaryl, aryl-$C_1$-$C_4$ alkyl, heteroaryl-$C_1$-$C_4$ alkyl, heterocyclyl-$C_1$-$C_4$ alkyl, or $R_1$ and $R_2$, together with the nitrogen atom to which they are attached, form N-heterocyclyl, aryl-N-heterocyclyl or heteroaryl-N-heterocyclyl;

each of said groups is optionally substituted with one or more substituents selected from the group consisting of $C_1$-$C_4$ alkyl, halogen, amino, $C_1$-$C_6$ alkyl amino, nitro, cyano, hydroxyl, hydroxyl $C_1$-$C_6$ alkyl, $C_1$-$C_6$ alkoxy, thiol and $C_1$-$C_6$ alkylthio;

or a pharmaceutically acceptable salt thereof.

2. The aminated homoharringtonine derivative or a pharmaceutically acceptable salt thereof according to claim 1, wherein $R_1$ and $R_2$ are independently selected from H, $C_1$-$C_6$ alkyl, $C_2$-$C_6$ alkenyl, $C_2$-$C_6$ alkynyl, $C_3$-$C_7$ cycloalkyl or cycloalkenyl, aryl, heterocyclyl, heteroaryl, aryl-$C_1$-$C_4$ alkyl, heteroaryl-$C_1$-$C_4$ alkyl, heterocyclyl-$C_1$-$C_4$ alkyl, or $R_1$ and $R_2$, together with the nitrogen atom to which they are attached, form N-heterocyclyl, aryl-N-heterocyclyl or heteroaryl-N-heterocyclyl; each of said groups is optionally substituted with one or more substituents selected from the group consisting of $C_1$-$C_4$ alkyl, halogen, amino, $C_1$-$C_6$ alkylamino, nitro, cyano, hydroxyl, hydroxyl-$C_1$-$C_6$ alkyl, $C_1$-$C_6$ alkoxy, thiol and $C_1$-$C_6$ alkylthio.

3. The aminated homoharringtonine derivative or a pharmaceutically acceptable salt thereof according to claim 1, wherein $R_1$ and $R_2$ are independently selected from H, $C_1$-$C_6$ alkyl, $C_3$-$C_7$ cycloalkyl, heteroaryl, heteroaryl-$C_1$-$C_4$ alkyl, or $R_1$ and $R_2$, together with the nitrogen atom to which they are attached, form N-heterocyclyl, aryl-N-heterocyclyl or heteroaryl-N-heterocyclyl with the nitrogen atoms to which they are connected; each of said groups is optionally substituted with one or more substituents selected from the group consisting of $C_1$-$C_4$ alkyl, halogen, amino, $C_1$-$C_6$ alkyl amino, nitro, cyano, hydroxyl, hydroxyl $C_1$-$C_6$ alkyl, $C_1$-$C_6$ alkoxy, thiol and $C_1$-$C_6$ alkylthio.

4. The aminated homoharringtonine derivative or a pharmaceutically acceptable salt thereof according to any one of claims 1-3, wherein said aryl is phenyl or naphthyl.

5. The aminated homoharringtonine derivative or a pharmaceutically acceptable salt thereof according to any one of claims 1-3, wherein said heteroaryl is furanyl, thiophenyl, pyrrolyl, thiazolyl, oxazolyl, isoxazolyl, pyrazolyl or pyridinyl; preferably furanyl, thiophenyl or thiazolyl.

6. The aminated homoharringtonine derivative or a pharmaceutically acceptable salt thereof according to any one of claims 1-3, wherein said heterocyclic radical or N-heterocyclyl is piperazinyl, morpholinyl, thiomorpholinyl, piperidyl, pyrrolidyl, pyrrolinyl, oxazolidinyl, isooxazolidinyl, thiazolidinyl, or pyrazolidinyl.

7. The homoharringtonine derivative or a pharmaceutically acceptable salt thereof according to any one of claims 1-3, wherein said $C_3$-$C_7$ cycloalkyl is cyclopropyl, cyclobutyl, cyclopentyl or cyclohexyl.

8. The homoharringtonine derivative or a pharmaceutically acceptable salt thereof according to any one of claims 1-3, wherein said substituent is selected from halogen, amino, $C_1$-$C_6$alkyl amino, nitro, cyano, hydroxyl $C_1$-$C_6$ alkyl, $C_1$-$C_6$ alkoxy, $C_1$-$C_6$ alkyl; preferably methyl, ethyl, isopropyl, methoxy, ethoxy, hydroxymethyl, hydroxyethyl, hydroxyl, nitro, cyano, fluorine or chlorine.

9. The homoharringtonine derivative or a pharmaceutically acceptable salt thereof according to claim 1, wherein $R_1$ and $R_2$ are independently selected from H, $C_3$-$C_7$ cycloalkyl such as cyclohexyl, heteroaryl-$C_1$-$C_4$ alkyl such as furfuryl or methyl furfuryl, or $R_1$ and $R_2$, together with the nitrogen atom to which they are attached, form N-heterocyclyl such as pyrrolidinyl, piperidyl or dimethylaminopiperidyl, or aryl-N-heterocyclyl such as 4-phenylpiperazin-1-yl or 4-(4-fluorophenyl)-piperazin-1-yl.

Some examples of the aminated or amidated homoharringtonine derivatives of the present invention are shown as follows. These examples are intended only for further illustrating the present invention but not to limit the scope of the present invention by any means.

BS-HH-008

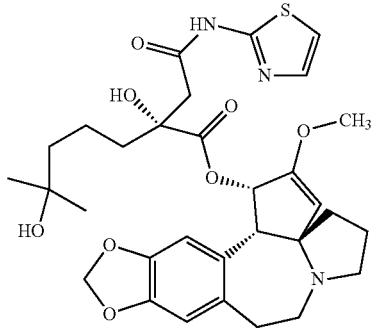

BS-HH-009

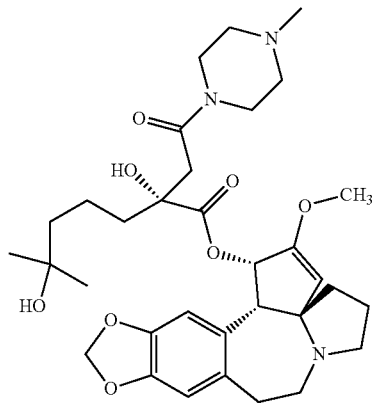

BS-HH-011

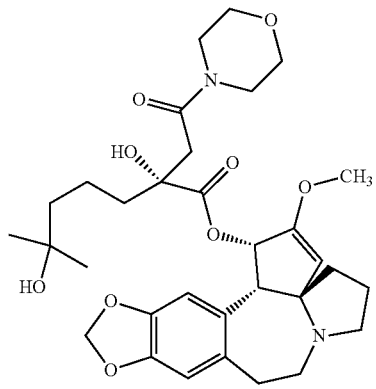

BS-HH-012

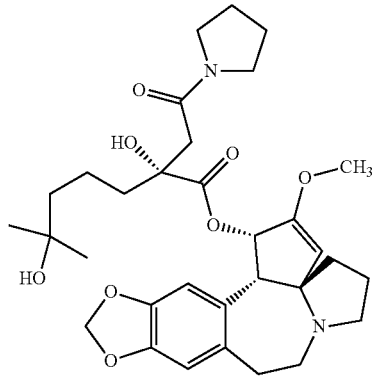

BS-HH-014

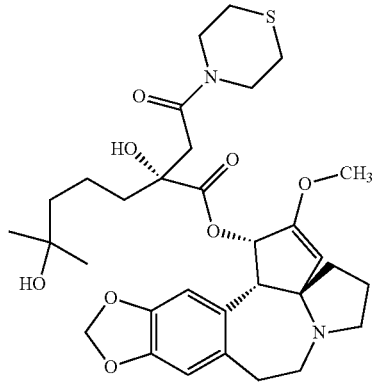

BS-HH-018
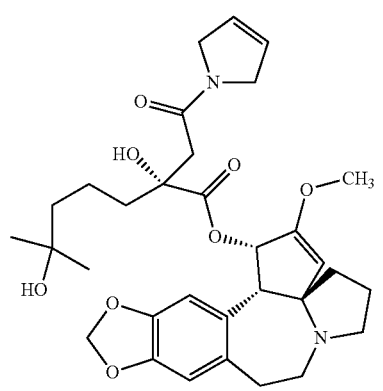
BS-HH-020
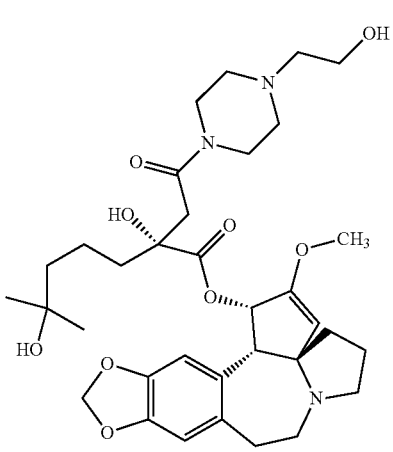
BS-HH-021
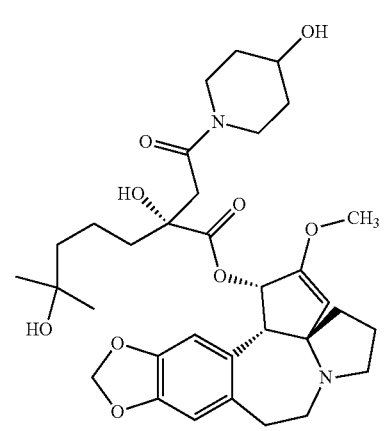
BS-HH-025
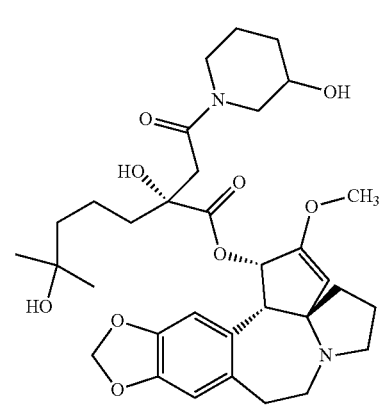
BS-HH-028
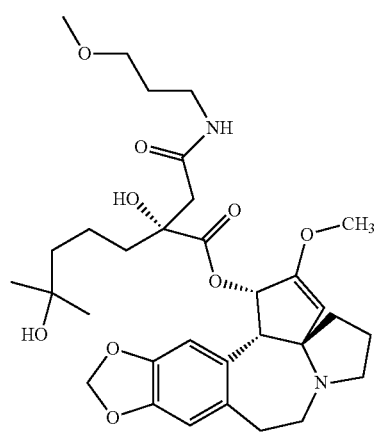
BS-HH-034
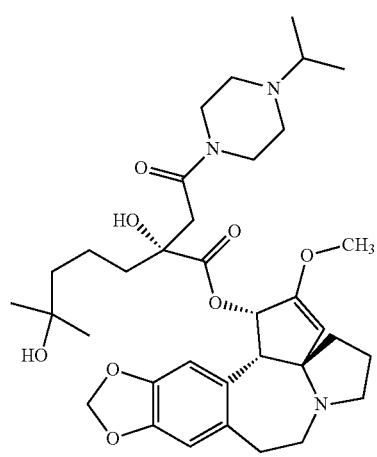
BS-HH-035
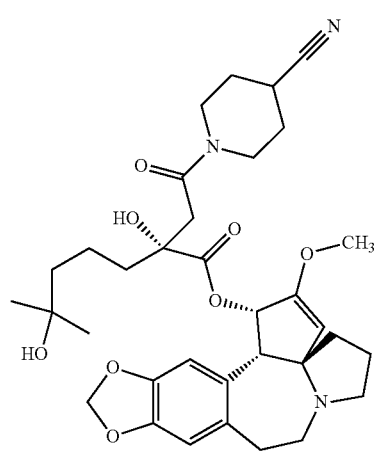

BS-HH-037
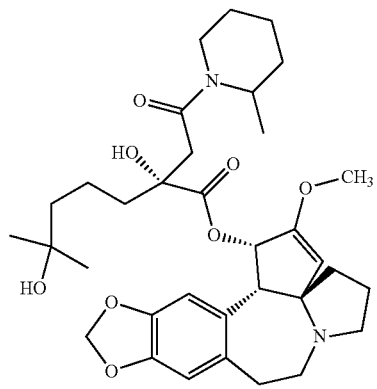
BS-HH-038
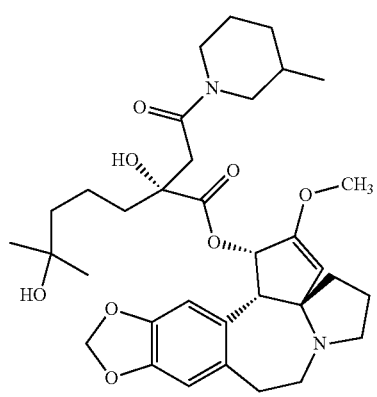
BS-HH-041
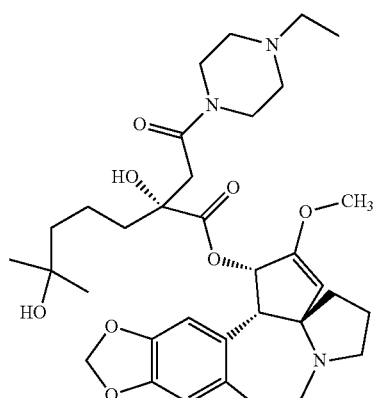
BS-HH-042
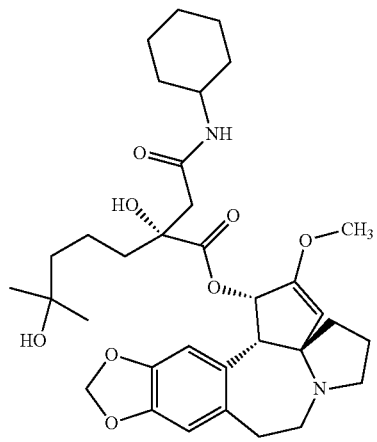
BS-HH-043
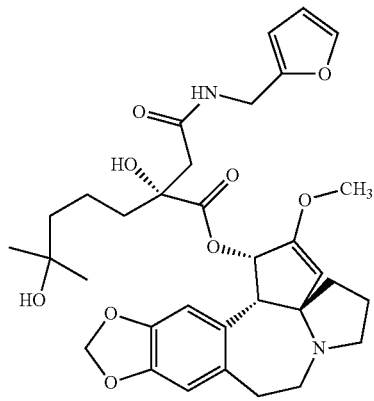
BS-HH-044
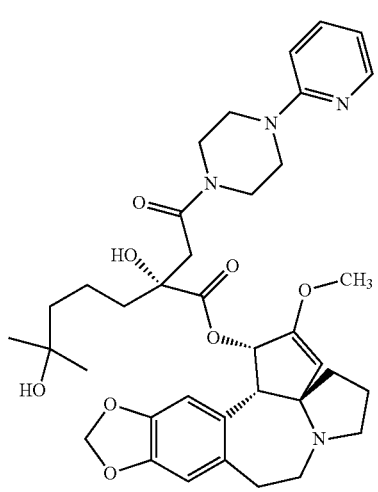
BS-HH-046
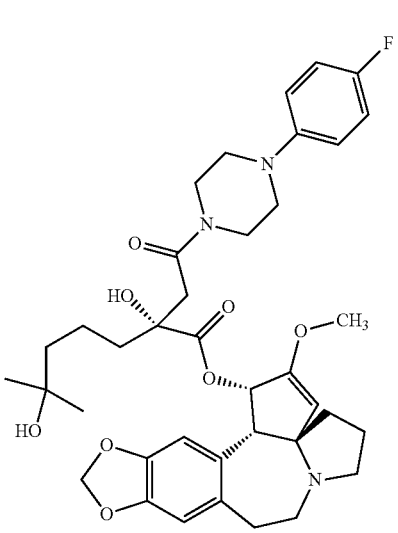

BS-HH-050

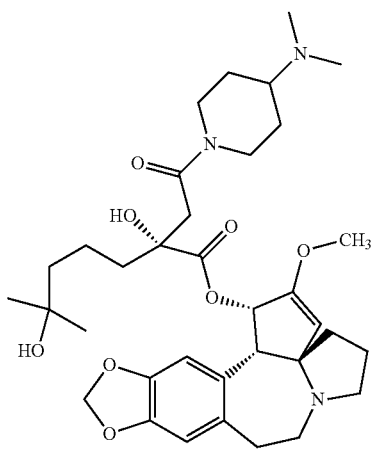

BS-HH-051

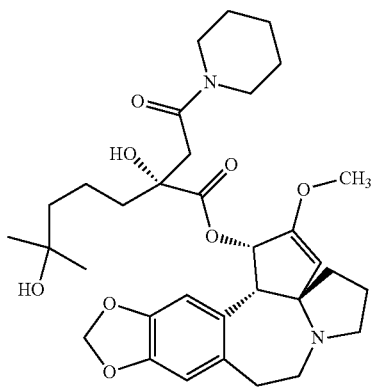

BS-HH-054

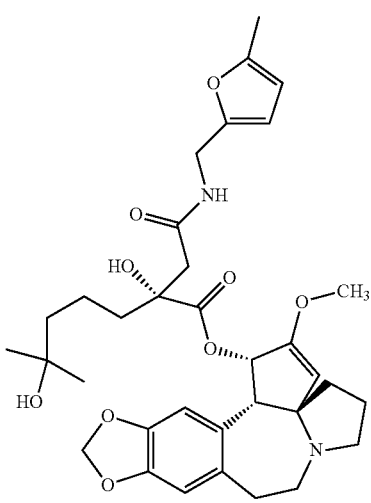

BS-HH-055

Some characterization data for the above compounds is listed in the following table:

| Compound No. | Molecular formula | Molecular weight | Appearance | State | Total yield of two-step reaction (%) |
|---|---|---|---|---|---|
| BS-HH-008 | $C_{31}H_{39}N_3O_8S$ | 613.7 | white | powder | 11 |
| BS-HH-009 | $C_{33}H_{47}N_3O_8$ | 613.7 | light yellow | viscous | 24 |
| BS-HH-011 | $C_{32}H_{44}N_2O_9$ | 600.7 | white | solid | 37 |
| BS-HH-012 | $C_{32}H_{44}N_2O_8$ | 584.7 | white | solid | 41 |
| BS-HH-014 | $C_{32}H_{44}N_2O_8S$ | 616.8 | white | solid | 44 |
| BS-HH-018 | $C_{32}H_{42}N_2O_8$ | 582.7 | white | solid | 43 |
| BS-HH-020 | $C_{34}H_{49}N_3O_9$ | 643.8 | white | solid | 34 |
| BS-HH-021 | $C_{33}H_{46}N_2O_9$ | 614.7 | white | solid | 42 |
| BS-HH-025 | $C_{33}H_{46}N_2O_9$ | 614.7 | white | solid | 39 |

| Compound No. | Molecular formula | Molecular weight | Appearance | State | Total yield of two-step reaction (%) |
|---|---|---|---|---|---|
| BS-HH-028 | $C_{32}H_{46}N_2O_9$ | 602.7 | light yellow | viscous | 11 |
| BS-HH-034 | $C_{35}H_{51}N_3O_8$ | 641.8 | white | solid | 38 |
| BS-HH-035 | $C_{34}H_{45}N_3O_8$ | 623.7 | white | solid | 41 |
| BS-HH-037 | $C_{34}H_{48}N_2O_8$ | 612.8 | yellowish brown | viscous | 27 |
| BS-HH-038 | $C_{33}H_{46}N_2O_8$ | 612.8 | light yellow | viscous | 38 |
| BS-HH-041 | $C_{34}H_{49}N_3O_8$ | 627.8 | light yellow | viscous | 33 |
| BS-HH-042 | $C_{34}H_{48}N_2O_8$ | 612.8 | light yellow | viscous | 32 |
| BS-HH-043 | $C_{33}H_{42}N_2O_9$ | 610.7 | white | oil | 6 |
| BS-HH-044 | $C_{37}H_{48}N_4O_8$ | 676.8 | light yellow | viscous | 37 |
| BS-HH-046 | $C_{38}H_{48}FN_3O_8$ | 693.8 | light yellow | solid | 42 |
| BS-HH-050 | $C_{35}H_{51}N_3O_8$ | 641.8 | yellow | viscous | 29 |
| BS-HH-051 | $C_{33}H_{46}N_2O_8$ | 598.7 | yellow | viscous | 34 |
| BS-HH-054 | $C_{34}H_{44}N_2O_9$ | 624.7 | light yellow | powder | 25 |
| BS-HH-055 | $C_{33}H_{42}N_2O_8S$ | 626.8 | light yellow | oil | 9 |

In another embodiment, the following compound of formula (I) is particularly preferred according to the present invention:

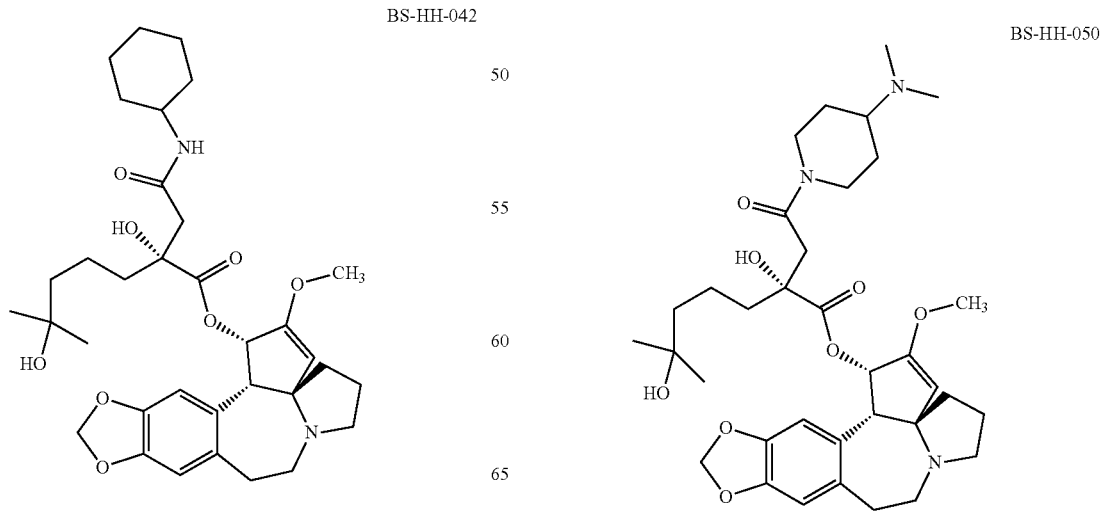

BS-HH-012

O-3-[(2R)-2,6-dihydroxy-2-(2'-pyrrolyl-2'-oxoethyl)-6-methylheptanoyl]cephalotaxine

BS-HH-042

BS-HH-046

O-3-[(2R)-2,6-dihydroxy-2-(2'-cyclohexaneamino-2'-oxoethyl)-6-methylheptanoyl]cephalotaxine O-3-[(2R)-2,6-dihydroxy-2-(2'-(4-(4-fluorophenyl)piperazinyl)-2'-oxoethyl)-6-methylheptanoyl]cephalotaxine

BS-HH-050

O-3-[(2R)-2,6-dihydroxy-2-(2'-(4-N,N-dimethylaminopiperidylpyrrolyl-2'-oxoethyl)-6-methylheptanoyl]cephalotaxine

BS-HH-054

O-3-[(2R)-2,6-dihydroxy-2-(2'-(5-methyl)furan-2-methylamino-2'-oxoethyl)-6-methylheptanoyl]cephalotaxine The present invention also relates to salts, solvates, hydrates, adducts, complexes, polymorphs or prodrugs of the compounds of formula (I) of the present invention.

As used herein, the term "alkyl" refers to a straight or branched hydrocarbon radical containing designated number of carbon atoms, such as $C_1$-$C_{18}$ alkyl, $C_1$-$C_6$ alkyl, $C_1$-$C_4$ alkyl, $C_1$-$C_3$ alkyl, etc. Examples of alkyl include, but not limited to, methyl, ethyl, n-propyl, isopropyl, tert-butyl, n-pentyl, n-hexyl, n-octadecyl, etc.

The term "alkenyl" refers to a straight or branched hydrocarbon radical containing designated number of carbon atoms and at least one carbon-carbon double bond, such as $C_2$-$C_{18}$ alkenyl, $C_2$-$C_{10}$ alkenyl, $C_2$-$C_8$ alkenyl, $C_2$-$C_7$ alkenyl, $C_2$-$C_6$ alkenyl, $C_2$-$C_4$ alkenyl, $C_2$-$C_3$ alkenyl, etc. Examples of alkenyl include, but not limited to, vinyl, allyl and octadecenyl.

The term "alkynyl" refers to a straight or branched hydrocarbon radical containing designated number of carbon atoms and at least one carbon-carbon triple bond, such as $C_2$-$C_{18}$ alkynyl, $C_2$-$C_{10}$ alkynyl, $C_2$-$C_8$ alkynyl, $C_2$-$C_7$ alkynyl, $C_2$-$C_6$ alkynyl, $C_2$-$C_4$ alkynyl, $C_2$-$C_3$ alkynyl, etc. Examples of alkynyl include, but not limited to, ethynyl, propargyl and octadecynyl.

The term "$C_3$-$C_7$ cycloalkyl or cycloalkenyl" refers to a saturated or unsaturated 3-7 membered monocyclic hydrocarbon radical. Representative examples of $C_3$-$C_7$ cycloalkyl can be cyclopropyl, cyclobutyl, cyclopentyl, cyclohexyl, cycloheptyl, cyclopropenyl and cyclohexenyl.

The term "aryl" refers to a monocyclic aryl or polycyclic aryl, fused or unfused, containing 6-14 carbon atoms. In the case of polycyclic aryl, at least one ring is aromatic. Aryl can also be one fused with a heterocyclic radical. Examples of aryl include phenyl, biphenyl, naphthyl, 5,6,7,8-tetrahydronaphthyl, 2,3-dihydrobenzofuranyl, etc.

The term "heteroaryl" refers to an aromatic ring group having 1-4 heteroatoms (e.g. 1, 2, 3 or 4 heteroatoms) in the ring as ring atom(s). A heteroatom refers to nitrogen, oxygen or sulfur. A heteroaryl can be a monocyclic heteroaryl having 5-7 ring atoms or a bicyclic heteroaryl having 7-11 ring atoms. Said bicyclic heteroaryl should comprise at least one aromatic heterocycle, and the other ring(s) can be aromatic or non-aromatic, with or without a heteroatom. Examples of heteroaryl include such as pyrrolyl, pyrazolyl, imidazolyl, oxazolyl, pyridinyl, pyrimidinyl, furanyl, thiophenyl, isoxazolyl, indolyl, etc.

"Heterocyclyl" refers to a non-aromatic cyclic group containing 1-4 heteroatoms (e.g. 1, 2, 3 or 4 heteroatoms) as ring atoms. A heteroatom refers to nitrogen, oxygen or sulfur. A heterocyclic radical can be a monocyclic heterocyclic radical having 4-8 ring atoms or a bicyclic heterocyclic radical having 7-11 ring atoms. A heterocyclic radical can be saturated, or can be unsaturated and meanwhile non-aromatic. Examples of heterocyclic radicals include azacyclobutyl, pyrrolidinyl, tetrahydrofuranyl, dihydrofuranyl, piperazinyl, piperidinyl, tetrahydropyranyl, tetrahydrothiophenyl, etc.

The term "halogen" refers to fluorine, chlorine, bromine or iodine.

The term "alkylamino" refers to an amino group substituted with one or two alkyl (including cycloalkyl) having designated number of carbon atoms.

The term "alkoxy" includes alkoxy and cycloalkyloxy.

The term "alkylthio" includes alkylthio and cycloalkylthio.

The term "pharmaceutically acceptable adducts and complexes of the compounds of formula (I)" refers to the product formed by a compound of the present invention with further combined small molecule or biological macromolecule via a non-chemical bond or non-covalent intermolecular force.

The term "pharmaceutically acceptable salts of the compounds of formula (I)" used herein is exemplified by the organic acid salts formed by an organic acid bearing a pharmaceutically acceptable anion. These organic acid salts include, but not limited to, tosylate, methanesulfonate, malate, acetate, citrate, malonate, tartrate, succinate, benzoate, ascorbate, α-ketoglutarate, and α-glycerophosphate. Suitable inorganic salts may also be formed, including but not limited to, hydrochloride, sulfate, nitrate, bicarbonate and carbonate, phosphate, hydrobromate, hydriodate salts and the like.

A pharmaceutically acceptable salt may be obtained using standard procedures well known in the art, for example by reacting a sufficient amount of alkaline compound with a suitable acid that provides a pharmaceutically acceptable anion.

As used herein, the term "polymorph" means a solid crystalline form of the compound of the present invention or a complex thereof. Various polymorphs of one same compound may exhibit different physical, chemical and/or spectroscopic properties. The different physical properties include, but not limited to, stability (e.g., thermal or light stability), compressibility and density (which are important for formulation and manufacture of the product), and dissolution rate (which may affect its bioavailability and absorbability). Differences in stability may result in a change in chemical reactivity (e.g., differential oxidation, such that a dosage form comprised of one polymorph discolors more rapidly than one comprised of another polymorph) or mechanical properties (e.g., in storage, crushed parts of the tablet of a kinetically favored polymorph is converted to a thermodynamically more stable polymorph) or both (e.g., tablets composed of one polymorph are more susceptible to breakdown at high humidity). Different physical properties of various polymorphs may affect their processing. For example, one polymorph may be more likely to form a solvate or may be more difficult to be filtered out or purified by washing than another one due to, for example, their different particle shapes or size distributions.

As used herein, the term "hydrate" means such a compound of the present invention or a salt thereof as further comprising a stoichiometric or non-stoichiometric amount of water bound via non-covalent intermolecular forces.

Unless otherwise indicated, the term "prodrug" used herein means a derivative of an inventive compound that, via hydrolyzation, oxidization, or other reactions under a biological condition (in vitro or in vivo), can provide a compound of this invention. A prodrug may only become active upon such a reaction under a biological condition, or may have activities in its unreacted form. Typically, a prodrug can be prepared using known methods, such as those described in Burger's Medicinal Chemistry and Drug Discovery (1995) 172-178, 949-982 (Manfred E. Wolff, 5$^{th}$ edition), Prodrugs and Targeted Delivery by J. Rautio (2011) 31-60 (Wiley-VCH, Methods and Principles in Medicinal Chemistry, Vol. 47), and Fundamentals of Medicinal Chemistry (2003) by G. Thomas, 195-200 (Wiley).

In the compounds of the present invention, the homoharringtonine derivatives have four chiral centers in the stereochemical structure represented by the structural formula (I). The stereochemical definitions and conventions used herein generally follow McGraw-Hill Dictionary of Chemical Terms (S. P. Parker, Ed., McGraw-Hill Book Company, New York, 1984); and Eliel, E. and Wilen, S., Stereochemistry of Organic Compounds (John Wiley & Sons, Inc., New York, 1994). Many organic compounds are present in optically active forms, i.e., they have the ability to rotate a plane of plane-polarized light.

The terms "treatment," "treating," "treat," and the like used herein refer generally to obtaining a desired pharmacological and/or physiological effect. The effect may be prophylactic in terms of completely or partially preventing a disease or symptoms thereof and/or may be therapeutic in terms of partial or complete stabilization or cure of a disease and/or adverse effects caused by the disease. "Treatment" as used herein covers any treatment of a disease in a subject, including: (a) preventing the disease or symptoms from occurring in a subject who is predisposed to the disease or symptoms but has not yet been diagnosed as having it; (b) inhibiting the symptoms of a disease, i.e., arresting its development; or (c) relieving the symptoms of a disease, i.e., causing regression of the disease or symptoms.

The compounds of the present invention can be prepared through a conventional organic chemistry synthesis process. For example, the compound of formula (I) of the present invention is prepared as follows.

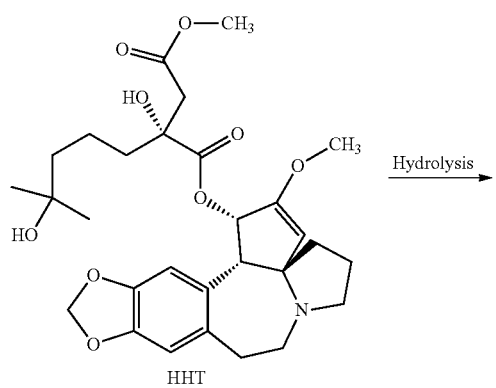

HHT

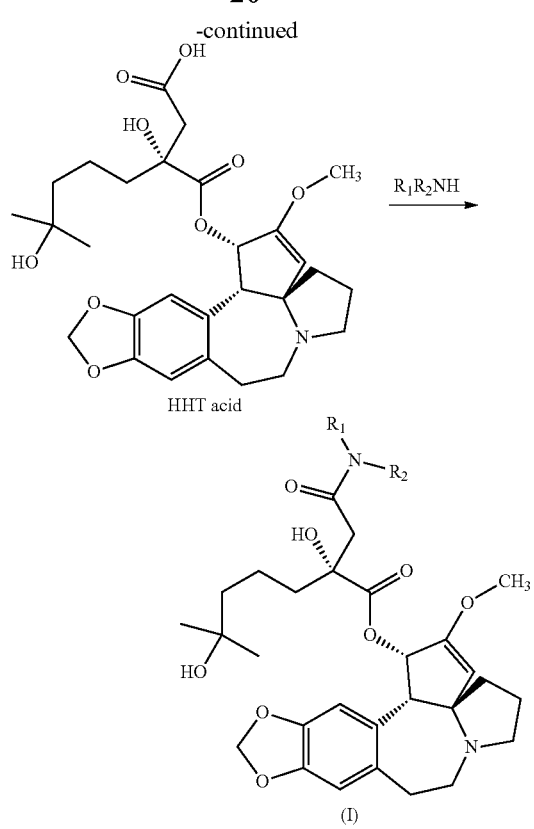

HHT acid (I)

The aminated homoharringtonine derivative of formula (I) can be prepared by firstly hydrolyzing extracted natural homoharringtonine (HHT) and then reacting it with appropriate organic amines via condensation. $R_1$ and $R_2$ in formula (I) are identical to those defined above for formula (I).

The above hydrolysis reaction typically takes place in the presence of an alkali or an alkaline reagent. The alkali herein can be, but not limited to, an inorganic alkali, such as sodium hydroxide, potassium hydroxide or lithium hydroxide.

The above hydrolysis reaction typically takes place in a solution. The solvents used herein include, but not limited to, polar solvents, such as methanol, water or the mixed solvent of methanol and water, etc.

The above hydrolysis reaction typically takes place under a temperature of 0° C.-40° C., which may varies with the alkali used or the concentration thereof.

The raw material for the hydrolysis reaction is homoharringtonine (HHT), which is obtained by extraction from natural products and is commercially available. The organic amines for the amination or amidation reaction can all be commercially available.

The hydrolysate of homoharringtonine, i.e. the acid as an intermediate, is subjected to condensation amination with appropriate organic amines in the presence of a condensation agent and an alkali to produce the aminated or amidated homoharringtonine derivatives of formula (I).

The amination or amindation reactions are carried out typically in the presence of a condensation agent. The condensation agent herein can be, but not limited to, organic condensation agents, such as 2-(7-azobenzotriazolyl)-N,N,N',N'-tetramethyluronium hexafluorophosphate (HATU), benzotriazolyl-N,N,N', N'-tetramethyluronium hexafluoroborate (HBTU), benzotriazol-1-yl-oxy-tris(dimethylamino)phosphonium hexafluorophosphate (BOP), and benzotriazolyl-N,N,N',N'-tetramethyluronium hexafluoroborate (TBTU).

The amination or amindation reactions are carried out typically in the presence of an alkali. The alkali herein can be, but not limited to, organic alkalis such as N,N-diisopropylethylamine (DIPEA), triethylamine (TEA), pyridine and 4-dimethylaminopyridine (DMAP).

The amination or amindation reactions are carried out typically in the presence or absence of a solvent. The solvent used herein includes, but not limited to, organic polar solvents such as dichloromethane (DCM), tetrahydrofuran (THF), N,N-dimethylformamide (DMF), dimethylsulfoxide (DMSO), etc.

The typical operation of the amination or amindation reactions can comprise, but not limited to, adding the reactants, the alkali and the condensation agent in a suitable proportion to DCM; stirring for 24 h under room temperature; extracting the resulted product with an organic solvent; washing it with water and saturated saline solution, drying and concentration to obtain the crude product; and purifying the crude product with HPLC to obtain the pure product.

Conventional chemical conversion processes may be used to practice this invention. One skilled person in the art can determine suitable chemical agents, solvents, protecting groups, and reaction conditions for these chemical conversions. Relevant information are described, for example, in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Protecting groups refer to the groups that, upon being attached to an active moiety (e.g., a hydroxyl or amino group), prevent the moiety from interference in a subsequent reaction and, after the reaction, can be removed through a conventional method. Examples of a hydroxyl protecting group include, but not limited to, alkyl, benzyl, allyl, trityl (also known as triphenylmethyl), acyl (e.g., benzoyl, acetyl, or HOOC—X"—CO—, wherein X" is alkylidene, alkenylene, cycloalkylene, or arylene), silyl (e.g., trimethylsilyl, triethylsilyl, and t-butyldimethylsilyl), alkoxylcarbonyl, aminocarbonyl (e.g., dimethylaminocarbonyl, methylethylaminocarbonyl, and phenylaminocarbonyl), alkoxymethyl, benzyloxymethyl, and alkylmercaptomethyl. Examples of an amino protecting group include, but not limited to, alkoxycarbonyl, alkanoyl, aryloxycarbonyl, aryl-substituted alkyl and the like. Hydroxyl and amino protecting groups have been discussed in T. W. Greene and P. G. M. Wuts, Protective Groups in Organic Synthesis, 2nd. Ed., John Wiley and Sons (1991). All hydroxyl and amino protecting groups can be removed by a conventional method after the reaction.

The present invention also provides a pharmaceutical composition comprising the compound of formula (I) of the present invention.

The present invention provides a pharmaceutical composition which comprises at least one compound of formula (I) of the present invention as defined above and optionally a pharmaceutically acceptable excipient.

The methods for preparing various pharmaceutical compositions having a given amount of active components are known or will be apparent to those skilled in the art in light of this disclosure. As described in REMINGTON'S PHARMACEUTICAL SCIENCES, Martin, E. W., ed., Mack Publishing Company, 19th ed. (1995), the methods for preparing such pharmaceutical compositions include incorporation of other suitable pharmaceutical excipients, carriers, diluents, etc.

The pharmaceutical preparations of the present invention are produced by known methods, including mixing, dissolving, or freeze drying processes.

The compounds of the present invention may be formulated into a pharmaceutical composition and administered to a subject in a route suitable for the selected administration manner, e.g., orally or parenterally (for example, by an intravenous, intramuscular, topical or subcutaneous route).

Thus, the present compounds may be systemically administered, e.g., orally administered, in conjugation with a pharmaceutically acceptable carrier such as an inert diluent or an edible carrier. They may be enclosed in hard or soft gelatin capsules, or may be compressed into tablets. For therapeutic oral administration, the active compound may be combined with one or more excipients and may be taken in a form of ingestible tablet, buccal tablet, troche, capsule, elixir, suspension, syrup, wafer, and the like. Such a composition or preparation should contain at least 0.1% of the active compound. Of course, the proportion of active compound in the compositions and preparations may vary and may be from about 1% to about 99% by weight of a given unit dosage form. In a therapeutically useful composition, the active compound is present in an amount such that an effective dosage level is achieved.

A tablet, troche, pill, capsule and the like may also comprise a binder, such as gum tragacanth, arabic gum, corn starch or gelatin; an excipient such as calcium dihydrogenphosphate; a disintegrating agent such as corn starch, potato starch, alginic acid and the like; a lubricant such as magnesium stearate; and a sweetening agent such as sucrose, fructose, lactose or aspartame; or a flavoring agent such as peppermint, wintergreen oil, or cherry flavor. In case the unit dosage form is a capsule, it may comprise, in addition to the above materials, a liquid vehicle such as a vegetable oil or polyethylene glycol. Various other materials may be present as coatings or otherwise modify the physical form of the solid unit dosage form. For instance, a tablet, pill, or capsule may be coated with gelatin, wax, shellac or sugar, etc. A syrup or elixir may contain an active compound, a sweetening agent such as sucrose or fructose, a preservative such as methylparaben or propylparaben, a dye and a flavoring agent (such as cherry or orange flavor). Of course, any materials used in preparing unit dosage forms should be pharmaceutically acceptable and substantially non-toxic in the amounts employed. In addition, the active compound may be incorporated into a sustained-release preparation or in a device.

The active compound may also be administered intravenously or intraperitoneally by infusion or injection. An aqueous solution of the active compound or its salt may be prepared, optionally mixed with a nontoxic surfactant. Also can be prepared is dispersion in glycerol, liquid polyethylene glycol, triacetin, or a mixture thereof, or in an oil. Under ordinary storage and use conditions, these preparations contain a preservative to prevent the growth of microorganisms.

The pharmaceutical dosage forms suitable for injection or infusion may include a sterile aqueous solution, a dispersion or a sterile powder comprising active ingredient (optionally encapsulated in liposomes), which are adapted for an extemporaneous preparation of a sterile injectable or infusible solution or dispersion. In all cases, the final dosage form must be sterile and stable liquids under the manufacture and storage conditions. The liquid carrier or vehicle may be a solvent or a liquid dispersion medium comprising, for example, water, ethanol, a polyol (for example, glycerol, propylene glycol, liquid polyethylene glycol, and the like), a vegetable oil, a nontoxic glyceryl ester, and a suitable mixture thereof. A proper fluidity can be maintained, for example, by formation of liposomes, by maintenance of the required particle size in the case of dispersion or by the use of a surfactant. The prevention of microorganism can be achieved by various antibacterial and antifungal agents, such as parabens, chlorobutanol, phenol, sorbic acid, thimerosal, and the like. In many cases, an isotonic agent is preferably comprised, such as sugar, buffer agent or sodium chloride. Prolonged absorption of an injectable composition can be obtained by the use of a composition of the agents for delaying absorption, for example, aluminum monostearate and gelatin.

An injectable sterile solution is prepared by combining a required amount of the active compound in a suitable solvent with various additional desired components as listed above, followed by filtration and sterilization. For sterile powder used to prepare an injectable sterile solution, the preferred preparation process is vacuum drying and freeze drying techniques, which yield a powder of the active ingredient plus any additional desired ingredient present in the previous filtered sterile solution.

Useful solid carriers include finely divided solids such as talc, clay, microcrystalline cellulose, silica, alumina and the like. Useful liquid carriers include water, ethanol or ethylene glycol or a water-ethanol/ethylene glycol mixture, in which the compound of the present invention can be dissolved or dispersed at an effective content, optionally with the aid of a non-toxic surfactant. An adjuvant (such as a flavour) and additional antimicrobial agent can be added to optimize the properties for a given application.

Thickening agent (such as a synthetic polymer, a fatty acid, a fatty acid salt and ester, a fatty alcohol, a modified cellulose or a modified inorganic material) can also be used with a liquid carrier to form a spreadable paste, gel, ointment, soap and the like for applying directly to the skin of a user.

The amount of the compound or an active salt or derivative thereof required for a treatment varies depending not only on the selected particular salt but also on the administration route, the nature of the condition to be treated and the age and condition of the subject, and will be ultimately determined at the discretion of the attendant physician or clinician.

The above formulations can be present in a unit dosage form which is a physically discrete unit containing a unit dosage, which is suitable for administering to a human or other mammalians. The unit dosage form may be a capsule or a tablet, or a plurality of capsules or tablets. Depending upon the intended particular therapy, the amount of the active ingredient in a unit dosage form can be varied or adjusted in the range of about 0.1 mg to about 1,000 mg or more.

The present invention also provides the use of a compound according to the present invention or a pharmaceutical composition comprising the compound of the present invention in manufacture of a medicament, especially an antitumor medicament. Accordingly, the present invention provides a method for treating a subject suffering from tumor, comprising administering to the subject in need thereof a therapeutically effective amount of at least one compound of the present invention. The homoharringtonine derivative of the present invention or a pharmaceutically acceptable salt thereof can be used, for example, for the treatment of leukemia, multiple myeloma, lymphoma, liver cancer, gastric cancer, breast cancer, cholangiocellular carcinoma, pancreatic cancer, lung cancer, colorectal cancer, osteosarcoma, melanoma, cervical cancer, glioma, nasopharyngeal carcinoma, laryngeal carcinoma, esophageal cancer, middle ear tumor, prostate cancer, etc.

The present invention will be explained in more detailed by the following examples. However, it should be understood that the following examples are intended for illustration only but not to limit the scope of the present invention in any way.

The raw chemicals used in the following examples are commercially available or may be obtained by a synthesis method known in the art.

The General Scheme and Process of the Amination Reaction:

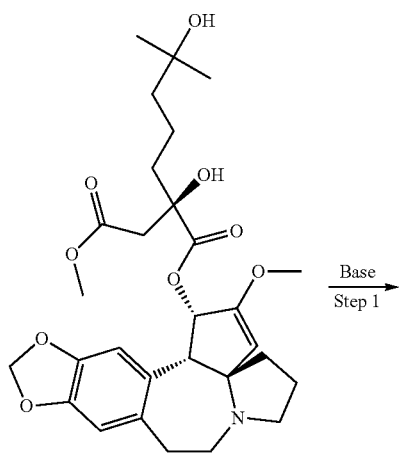

HHT

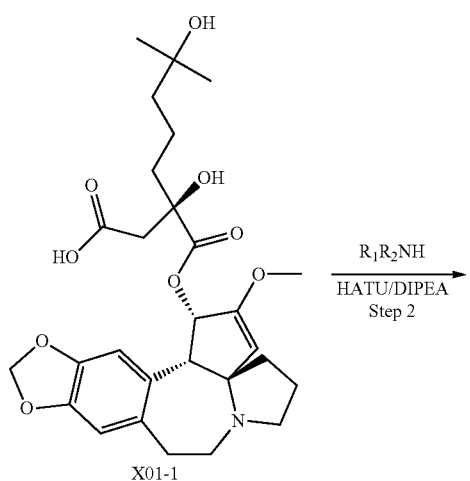

X01-1

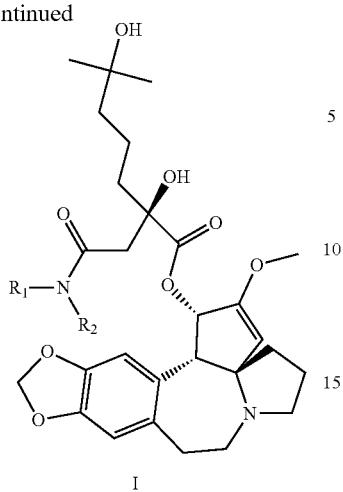

I

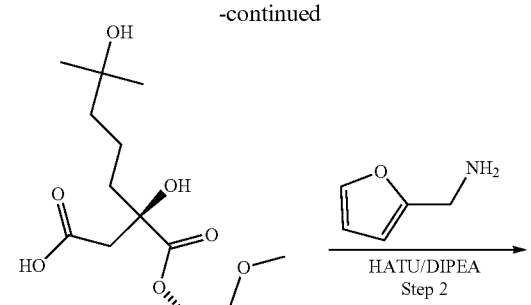

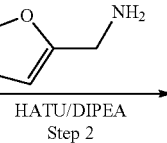

X01-1

Homoharringtonine (HHT, 2.5 g, 4.58 mmol) is dissolved in methanol (18 mL), in which an alkaline solution (1 M, 4.6 mL) is added, wherein the alkali can be either sodium hydroxide or lithium hydroxide. The mixture is stirred for 7 h under room temperature and the pH of the reacting solution is adjusted to 5-7 with an acid solution (1 N), wherein the acid can be either HCl or another inorganic acid. Organic solvent is removed by concentration. The resulted aqueous solution is treated several times with toluene, concentrated and dried to obtain a homoharringtonine acid (2.5 g, 88% of purity) as a white solid. The rest 5% of raw materials can be recycled, followed by hydrolysis again.

The homoharringtonine acid X01-1(1.0 eq) and an amine (1.0-1.5 eq) are dissolved in anhydrous DMF (20-50 eq), in which N,N-diisopropyl-ethylamine (2.0 eq) and 2-(7-azobenzotriazolyl)-N,N,N',N'-tetramethyluronium hexafluorophosphate (1.5 eq) are also added. After stirring for 2 h under room temperature, water is added to the reacting Solution, followed by extraction with ethyl acetate. The organic phase is washed with a saturated saline solution, dried and concentrated. The resulted crude product is purified with HPLC to obtain 2'-aminated homoharringtonine.

Example 1

The Synthesis of Compound BS-HH-043

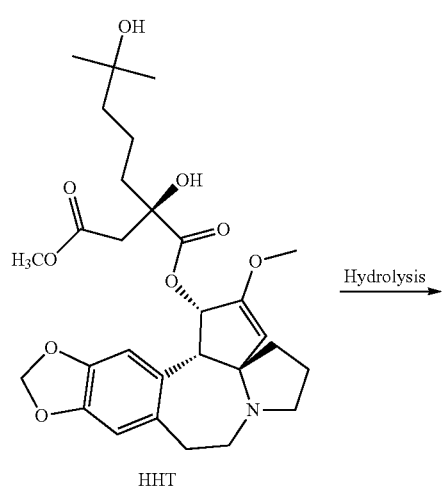

HHT

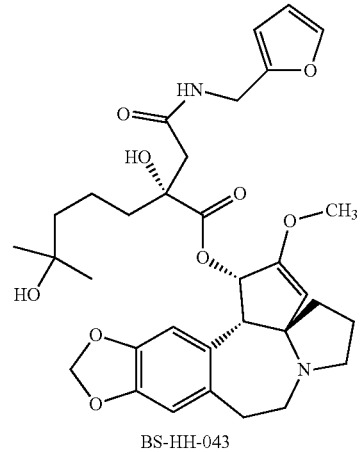

BS-HH-043 wherein, X01-1: homoharringtonine acid; HATU: 2-(7-azobenzotriazolyl)-N,N,N',N'-tetramethyluronium hexafluorophosphate; DIPEA: N,N-diisopropylethylamine.

Homoharringtonine is hydrolyzed according to the general scheme above. Afterwards, the acid resulted from the hydrolysis of homoharringtonine, as an intermediate, X01-1(106 mg, 0.2 mmol), and 2-aminomethylfuran (24 mg, 0.24 mmol) are dissolved in anhydrous DMF (2 mL). N,N-diisopropylethylamine (52 mg, 0.4 mmol) and 2-(7-azobenzotriazolyl)-N,N,N',N'-tetramethyluronium hexafluorophosphate (114 mg, 0.3 mmol) are added and the mixture is stirred for 3 h under 30° C. Water (6 mL) is added under 5-10° C. and the mixture is extracted with ethyl acetate. The organic phase is washed with a saturated saline solution, dried and concentrated. The crude product is separated and purified with a silicagel column (DCM: methanol=10:1) to give BS-HH-043 (9 mg, 6%) as a colorless oil product.

LC-MS: retention time: 1.18 min (60.6%), m/z: 611.4 [M+H]$^+$.

$^1$H NMR (300 MHz, CDCl$_3$): δ 7.34 (s, 1H), 6.67 (s, 1H), 6.58 (s, 1H), 6.31 (d, 1H), 6.20 (d, 1H), 5.94-5.87 (m, 3H), 4.34 (m, 2H), 3.81 (s, 1H), 3.71 (s, 3H), 2.02 (m, 3H), 1.17 (s, 6H).

BS-HH-008 is obtained according to the process in Example 1 using the same coupling reagent by reacting acid intermediate resulted from the hydrolysis of homoharringtonine, X01-1, with 2-aminothiazole.

LC-MS: retention time: 1.09 min (90.35%), m/z: 614.5 [M+H]$^+$.

BS-HH-009 is obtained according to the process in Example 1 by reacting the acid intermediate resulted from the hydrolysis of homoharringtonine, X01-1, with 1-methylpiperazine in the presence of the same coupling reagent as above.

LC-MS: retention time: 1.08 min (94.6%), m/z: 308.2 [1/2M+H]$^+$.

$^1$H NMR (300 MHz, CDCl$_3$): δ 6.60 (s, 1H), 6.59 (s, 1H), 5.95 (m, 2H), 5.80-5.8 (s, 1H), 5.02 (s, 1H), 4.49 (s, 1H), 3.78 (d, J=12.0Hz, 1H), 3.68 (s, 3H), 3.13-3.39 (m, 4H), 2.95 (m, 1H), 2.39 (m, 2H), 2.28 (s, 3H), 2.26-2.16 (m, 4H), 1.69 (m, 6H), 1.18 (d, 6H).

BS-HH-011 is obtained according to the process in Example 1 by reacting the acid intermediate resulted from the hydrolysis of homoharringtonine, X01-1, with morpholine in the presence of the same coupling reagent.

LC-MS: retention time: 1.05 min (90.03%), m/z: 601.3 [M+H]$^+$.

$^1$H NMR (300 MHz, CDCl$_3$): δ 6.60 (d, 2H), 5.97 (m, 2H), 5.81 (s, 1H), 5.02 (s, 1H), 4.31 (s, 1H), 3.79 (d, 1H), 3.68 (s, 3H), 3.57 (m, 2H), 2.59(m, 2H), 2.38 (m, 1H), 2.00 (s, 3H), 1.05 (s, 6H).

BS-HH-012 is obtained according to the process in Example 1 by reacting the acid intermediate resulted from the hydrolysis of homoharringtonine, X01-1, with pyrrolidine in the presence of the same coupling reagent.

LC-MS: retention time: 1.14 min (95.15%), m/z: 585.4 [M+H]$^+$.

$^1$H NMR (300 MHz, CDCl$_3$): δ 6.60 (d, 2H), 5.89 (m, 2H), 5.79 (s, 1H), 5.01 (s, 1H), 4.76 (s, 1H), 3.78 (d, 1H), 3.68 (s, 3H), 3.36 (m, 2H), 3.27-3.01 (m, 4H), 2.59(m, 2H), 2.38 (m, 1H), 1.18 (s, 6H).

BS-HH-014 is obtained according to the process in Example 1 by reacting the acid intermediate resulted from the hydrolysis of homoharringtonine, X01-1, with thiomorpholine in the presence of the same coupling reagent.

LC-MS: retention time: 1.17 min (100%), m/z: 617.4 [M+H]$^+$.

$^1$H NMR (300 MHz, CDCl$_3$): δ 6.58 (d, 2H), 6.00 (m, 2H), 5.80(s, 1H), 5.02 (s, 1H), 4.32 (s, 1H), 3.75 (d, J=9 Hz, 1H), 3.68 (s, 3H), 3.48 (m, 2H), 2.95 (m, 1H), 2.37 (m, 1H), 2.23 (d, 1H), 1.19 (s, 6H).

BS-HH-018 is obtained according to the process in Example 1 by reacting the acid intermediate resulted from the hydrolysis of homoharringtonine, X01-1, with 2,5-dihydropyrrole in the presence of the same coupling reagent as above.

LC-MS: retention time: 1.08 min (100%), m/z: 583.3 [M+H]$^+$.

$^1$H NMR (300 MHz, CDCl$_3$): δ 6.60 (s, 1H), 6.58 (s, 1H), 6.02 (d, J=9 Hz, 1H), 5.85 (m, 2H), 5.78 (m, 2H), 5.01 (s, 1H), 4.37 (s, 1H), 3.78 (d, 1H), 3.67 (s, 3H), 2.56 (m, 2H), 2.38 (m, 1H), 2.24 (d, 1H), 2.00 (s, 3H), 1.19 (s, 6H).

BS-HH-020 is obtained according to the process in Example 1 by reacting the acid intermediate resulted from the hydrolysis of homoharringtonine, X01-1, with 2-(piperazin-1-yl)ethanol in the presence of the same coupling reagent.

LC-MS: retention time: 0.91 min (96.62%), m/z: 644.5 [M+H]$^+$.

$^1$H NMR (300 MHz, CDCl$_3$): δ 6.59 (d, 2H), 5.93 (m, 2H), 5.80 (s, 1H), 5.02 (s, 1H), 4.43 (s, 1H), 3.79 (d, 1H), 3.68 (s, 3H), 3.61 (m, 2H), 2.95 (m, 1H), 2.61-2.54 (m, 5H), 2.00 (m, 4H), 1.32 (m, 6H), 1.18 (s, 6H).

BS-HH-021 is obtained according to the process in Example 1 by reacting the acid intermediate resulted from the hydrolysis of homoharringtonine, X01-1, with 4-hydroxypiperidine in the presence of the same coupling reagent as above.

LC-MS: retention time: 1.02 min (98.13%), m/z: 615.4 [M+H]$^+$.

$^1$H NMR (300 MHz, CDCl$_3$): δ 6.60 (s, 1H), 6.58 (s, 1H), 5.99-5.90 (m, 2H), 5.80 (s, 1H), 5.01 (s, 1H), 4.54 (d, 1H), 3.78 (d, 1H), 3.68 (s, 3H), 2.61 (m, 2H), 2.39 (m, 1H), 2.26 (m, 2H), 1.18 (s, 6H).

BS-HH-025 is obtained according to the process in Example 1 by reacting the acid intermediate resulted from the hydrolysis of homoharringtonine, X01-1, with 3-hydroxypiperidine in the presence of the same coupling reagent as above.

LC-MS: retention time: 1.04 min (97.26%), m/z: 615.3 [M+H]$^+$.

$^1$H NMR (300 MHz, CDCl$_3$): δ 6.61 (d, 2H), 5.90 (m, 2H), 5.81 (s, 1H), 5.02 (s, 1H), 4.60 (s, 1H), 3.76 (d, 1H), 3.68 (s, 3H), 2.63-2.56 (m, 2H), 2.36 (m, 1H), 1.18 (s, 6H).

BS-HH-028 is obtained according to the process in Example 1 by reacting the acid intermediate resulted from the hydrolysis of homoharringtonine, X01-1, with 3-methoxypropylamine in the presence of the same coupling reagent as above.

LC-MS: retention time: 1.06 min (69.32%), m/z: 603.8 [M+H]$^+$.

BS-HH-034 is obtained according to the process in Example 1 by reacting the acid intermediate resulted from the hydrolysis of homoharringtonine, X01-1, with 1-isopropylpiperazine in the presence of the same coupling reagent as above.

LC-MS: retention time: 0.95 min (98.32%), m/z: 642.4 [M+H]$^+$.

$^1$H NMR (300 MHz, CDCl$_3$): δ 6.58 (d, 2H), 5.95 (m, 2H), 5.82 (d, 1H), 5.01 (s, 1H), 4.56 (s, 1H), 3.79 (d, 1H), 3.68 (s, 3H), 2.72 (m, 1H), 2.55 (m, 4H), 2.36 (m, 3H), 2.25 (s, 2H), 2.00 (s, 3H), 1.31 (m, 6H), 1.18 (s, 6H), 1.01 (d, 6H).

BS-HH-035 is obtained according to the process in Example 1 by reacting the acid intermediate resulted from the hydrolysis of homoharringtonine, X01-1, with 4-cyanopiperidine in the presence of the same coupling reagent as above.

LC-MS: retention time: 1.11 min (99.31%), m/z: 624.3 [M+H]$^+$.

$^1$H NMR (300 MHz, CDCl$_3$): δ 6.61 (d, 2H), 5.9 (m, 2H), 5.79 (d, 1H), 5.01 (s, 1H), 4.30 (d, 1H), 3.67 (s, 3H), 3.35 (m, 2H), 2.59 (m, 2H), 2.38 (m, 1H), 2.24 (m, 1H), 2.16 (d, 1H), 1.66-1.87 (m, 4H), 1.19 (s, 6H).

BS-HH-037 is obtained according to the process in Example 1 by reacting the acid intermediate resulted from the hydrolysis of homoharringtonine, X01-1, with 2-methylpiperidine in the presence of the same coupling reagent as above.

LC-MS: retention time: 1.59 min (98.91%), m/z: 613.6 [M+H]$^+$.

$^1$H NMR (300 MHz, CDCl$_3$): δ 6.60 (d, 2H), 5.88 (m, 2H), 5.82 (s, 1H), 5.02 (s, 1H), 4.41 (d, 1H), 3.80 (d, 1H), 3.69 (s, 3H), 2.59 (m, 2H), 2.38 (m, 1H), 1.18 (s, 6H).

BS-HH-038 is obtained according to the process in Example 1 by reacting the acid intermediate resulted from the hydrolysis of homoharringtonine, X01-1, with 3-methylpiperidine in the presence of the same coupling reagent as above.

LC-MS: retention time: 1.57 min (98.69%), m/z: 613.6 [M+H]$^+$.

¹H NMR (300 MHz, CDCl₃): δ 6.59 (d, 2H), 5.97-5.88 (m, 2H), 5.81 (m, 1H), 5.02 (d, 1H), 4.64 (m, 1H), 3.80 (m, 1H), 3.69 (s,3H), 2.59 (m, 2H), 2.28 (m, 2H), 1.18 (d, 6H), 0.92-0.84 (m,3 H).

BS-HH-041 is obtained according to the process in Example 1 by reacting the acid intermediate resulted from the hydrolysis of homoharringtonine, X01-1, with 1-ethyl-piperazine in the presence of the same coupling reagent as above.

LC-MS: retention time: 1.08 min (100%), m/z: 628.6 [M+H]⁺.

¹H NMR (300 MHz, CDCl₃): δ 6.58 (d, 2H), 5.94 (m, 2H), 5.80 (s, 1H), 5.01 (s, 1H), 3.77 (d, 1H), 3.68 (s, 3H), 3.35-3.05 (m, 4H), 1.75 (m, 4H), 1.18 (s, 6H), 1.07 (t, 3H).

BS-HH-042 is obtained according to the process in Example 1 by reacting the acid intermediate resulted from the hydrolysis of homoharringtonine, X01-1, with 2-aminomethylfuran in the presence of the same coupling reagent as above.

LC-MS: retention time: 1.57 min (85.35%), m/z: 613.6 [M+H]⁺.

¹H NMR (300 MHz, CDCl₃): δ 6.66 (d, 2H), 5.97-5.88 (m, 3H), 4.91 (s, 1H), 4.74 (d, 1H), 3.78 (s, 3H), 3.48 (m, 2H), 3.19 (m, 2H), 2.90 (m, 2H), 1.88 (m, 4H), 1.20-1.17 (m, 10H).

BS-HH-044 is obtained according to the process in Example 1 by reacting the acid intermediate resulted from the hydrolysis of homoharringtonine, X01-1, with 1-(pyridin-2-yl)piperazine in the presence of the same coupling reagent as above.

LC-MS: retention time: 1.17 min (100%), m/z: 677.6 [M+H]⁺.

¹H NMR (300 MHz, CDCl₃): δ 8.20 (dd, J=4.8 Hz, 1.2 Hz, 1H), 7.50 (m, 1H), 6.68-6.63 (m, 2H), 6.60 (d, 2H), 5.96 (d, 1H), 5.81 (s, 1H), 5.74 (s, 1H), 5.02 (s, 1H), 4.39 (s, 1H), 3.83-3.73 (m, 3H), 3.68 (s, 3H), 3.45-3.30 (m, 5H), 2.63-2.56 (m, 2H), 1.19 (s, 6H).

BS-HH-046 is obtained according to the process in Example 1 by reacting the acid intermediate resulted from the hydrolysis of homoharringtonine, X01-1, with 1-(4-fluorophenyl)piperazine in the presence of the same coupling reagent as above.

LC-MS: retention time: 1.61 min (89.27%), m/z: 694.6 [M+H]⁺.

¹H NMR (300 MHz, CDCl₃): δ 6.98 (m, 2H), 6.85 (m, 2H), 6.61 (d, 2H), 5.98 (d, 1H), 5.88 (d, 1H), 5.78 (d, 1H), 5.02 (s, 1H), 4.36 (s, 1H), 3.79 (d, 1H), 3.68 (s, 3H), 3.44 (m, 3H), 3.12 (m, 4H), 2.93 (m, 2H), 2.59 (s, 1H), 1.19 (s, 6H).

BS-HH-050 is obtained according to the process in Example 1 by reacting the acid intermediate resulted from the hydrolysis of homoharringtonine, X01-1, with 4-(N,N-methylamino)piperidine in the presence of the same coupling reagent as above.

LC-MS: retention time: 1.10 min (90.31%), m/z: 642.6 [M+H]⁺.

¹H NMR (300 MHz, CDCl₃): δ 6.59 (d, 2H), 5.98-5.86 (m, 2H), 5.80 (m, 1H), 5.02 (m, 1H), 3.80 (m, 1H), 3.69 (s, 3H), 3.57 (s, 1H), 2.59 (m, 3H), 2.28 (d, 6H), 1.71 (m, 8H), 1.19 (s, 6H).

BS-HH-051 is obtained according to the process in Example 1 by reacting the acid intermediate resulted from the hydrolysis of homoharringtonine, X01-1, with piperidine in the presence of the same coupling reagent as above.

LC-MS: retention time: 1.48 min (98.45%), m/z: 599.5 [M+H]⁺.

¹H NMR (300 MHz, CDCl₃): δ 6.59 (d, 2H), 5.95-5.81 (m, 3H), 5.01 (s, 1H), 4.72 (s, 1H), 3.78 (d, 1H), 3.68 (s, 3H), 3.25-2.90 (m, 6H), 2.59 (m, 2H), 2.40 (m, 1H), 2.26 (s, 1H), 1.69 (m, 6H), 1.18 (s, 6H).

BS-HH-054 is obtained according to the process in Example 1 by reacting the acid intermediate resulted from the hydrolysis of homoharringtonine, X01-1, with 5-methyl-2-aminomethylfuran in the presence of the same coupling reagent as above.

LC-MS: retention time: 1.23 min (63.39%), m/z: 625.8 [M+H]⁺.

¹H NMR (300 MHz, CDCl₃): δ 6.73 (s, 1H), 6.62 (s, 1H), 6.06-5.89 (m, 4H), 4.30 (s, 1H), 3.78 (s, 3H), 2.26 (s, 3H), 1.33 (s, 6H).

BS-HH-055 is obtained according to the process in Example 1 by reacting the acid intermediate resulted from the hydrolysis of homoharringtonine, X01-1, with 2-aminomethylthiophene in the presence of the same coupling reagent as above.

LC-MS: retention time: 1.21 min (83.64%), m/z: 627.8 [M+H]⁺.

Example 2

Evaluation of the Aminated Homoharringtonine Derivatives of the Present Invention for Their Anti-Leukemia Activities (1) Experimental Materials Leukemia cell lines: K562/adr (drug-resistant, chronic myeloid leukemia, CML), NB4 (acute promyelocytic leukemia, AML), Kasumi-1 (acute myeloid leukemia M2 type, AML-M2), Jurkat (acute lymphoblastic leukemia, ALL), all of which are donated by Cancer Research Institute of Zhejiang University, China; and H9 (acute lymphoblastic leukemia, ALL), which is purchased from China Center for Type Culture Collection.

Reagents: The standard sample of homoharringtonine (HHT) is purchased from Taihua Natural Plant Pharmaceutical Co., Ltd., Shaanxi, China; and the homoharringtonine derivatives of the present invention.

Main apparatuses: a Thermo Scientific 3111 incubator and a Bio-Rad iMark microplate reader.

(2) Experimental Method

Obtaining 6000 well-growing leukemia cells and inoculating them into wells of a 96-well cell culture plate. The culture medium is the 1640 cell culture medium containing 10% fetal bovine serum. After adding the homoharringtonine derivatives of different concentrations and mixing uniformly, placing the plate in a carbon dioxide cell incubator (5% $CO_2$) at 37° C. and incubating for 72 hours. Then the viable cell concentration is determined by the MTT method. In this experiment, the cell viability in control group (not treated with any compound) is set as 100%. On such basis, the cell viability (%) after treatment and the half maximal inhibitory concentration of the compound for the leukemia cell growth at 72 hours ($IC_{50}$ value of 72 hours) are calculated.

(3) The Experimental Results

The experimental results are shown in table 1. Table 1 shows that the aminated homoharringtonine derivatives of the present invention can induce the cell death of human chronic myeloid leukemia cells, acute myeloid leukemia cells and acute lymphocytic leukemia cells and inhibit the growth of these leukemia cells. The aminated homoharringtonine derivatives of the present invention BS-HH-012, BS-HH-042, BS-HH-050 and BS-HH-054, have demonstrated strong anti-K562/adr (drug-resistant, chronic myeloid leukemia, CML), anti-NB4 (acute promyelocytic leukemia, AML), anti-Kasumi-1 (acute myeloid leukemia M2 type, AML-M2) and anti-H9 (acute lymphoblastic leukemia, ALL) activity.

TABLE 1

Determination of the inhibiting concentrations of the aminated homoharringtonine derivatives on leukemia cell growth (72 h, $IC_{50}$ (μg/mL) value and $IC_{90}$ (μg/mL) value)

|          | K562/adr | | Kasumi-1 | | NB4 | |
|----------|----------|------|----------|------|--------|-------|
| Compound | $IC_{50}$ | $IC_{90}$ | $IC_{50}$ | $IC_{90}$ | $IC_{50}$ | $IC_{90}$ |
| HHT      | 0.035 | 0.98 | 0.005 | 0.024 | 0.006 | 0.012 |
| BS-HH-008 | >16 | >16 | 5 | >16 | 5.62 | 12.83 |
| BS-HH-009 | >16 | >16 | 8.54 | >16 | 2.97 | 11.2 |
| BS-HH-011 | >16 | >16 | 8.28 | >16 | 3.22 | 9.54 |
| BS-HH-012 | 0.65 | 9.87 | 0.038 | 0.14 | 0.08 | 0.23 |
| BS-HH-014 | >16 | >16 | 1.33 | 8.61 | 1.29 | 3.7 |
| BS-HH-018 | 7.77 | >16 | 0.47 | 2.32 | 0.38 | 1 |
| BS-HH-020 | >16 | >16 | >16 | >16 | 7.46 | 15.79 |
| BS-HH-021 | >16 | >16 | 14.58 | >16 | 8 | 16 |
| BS-HH-025 | >16 | >16 | >16 | >16 | 8.31 | >16 |
| BS-HH-028 | >16 | >16 | 2.75 | 13 | 2.59 | 7.52 |
| BS-HH-034 | 4.53 | 16 | 0.31 | 1.77 | 0.48 | 2.3 |
| BS-HH-035 | 14.1 | >16 | 0.8 | 2.96 | 0.72 | 6.3 |
| BS-HH-037 | >16 | >16 | 1.58 | 16 | 0.7 | 5.08 |
| BS-HH-038 | >16 | >16 | 2 | 12.02 | 0.32 | 4.24 |
| BS-HH-041 | >16 | >16 | 2.79 | 14.99 | 1.85 | 16 |
| BS-HH-042 | 3.2 | 16 | 0.048 | 0.21 | 0.06 | 0.13 |
| BS-HH-043 | >16 | >16 | 11.06 | >16 | 15 | >16 |
| BS-HH-044 | 5.18 | 16 | 0.38 | 2.25 | 0.25 | 0.64 |
| BS-HH-046 | 14.5 | >16 | 0.26 | 2.26 | 0.19 | 0.5 |
| BS-HH-050 | 0.72 | 8.99 | 0.041 | 0.18 | 0.08 | 0.17 |
| BS-HH-051 | >16 | >16 | 2 | 16 | 1.5 | 16 |
| BS-HH-054 | 0.66 | 4.4 | 0.053 | 0.19 | 0.09 | 0.2 |
| BS-HH-055 | 6.24 | 16 | 1.3 | 6.68 | 2.38 | 7.61 |

|          | Jurkat | | H9 | |
|----------|--------|------|------|------|
| Compound | $IC_{50}$ | $IC_{90}$ | $IC_{50}$ | $IC_{90}$ |
| HHT | 0.007 | 16 | 0.02 | 0.046 |
| BS-HH-008 | 4.69 | 16 | 13.43 | >16 |
| BS-HH-009 | 3 | >16 | 8 | >16 |
| BS-HH-011 | 6.7 | >16 | >16 | >16 |
| BS-HH-012 | 0.058 | 16 | 0.27 | 3.49 |
| BS-HH-014 | 2 | >16 | 8.25 | >16 |
| BS-HH-018 | 0.88 | 16 | 2.69 | >16 |
| BS-HH-020 | 15.14 | >16 | >16 | >16 |
| BS-HH-021 | 13.4 | >16 | >16 | >16 |
| BS-HH-025 | >16 | >16 | >16 | >16 |
| BS-HH-028 | 3.56 | 15.04 | 6.52 | >16 |
| BS-HH-034 | 0.46 | 16 | 0.6 | 2.7 |
| BS-HH-035 | 0.87 | >16 | 5.49 | >16 |
| BS-HH-037 | 0.41 | >16 | 3.69 | >16 |
| BS-HH-038 | 1.47 | 16 | 7.37 | >16 |
| BS-HH-041 | 0.89 | >16 | 3.2 | >16 |
| BS-HH-042 | 0.037 | 16 | 0.04 | 0.1 |
| BS-HH-043 | 13 | >16 | >16 | >16 |
| BS-HH-044 | 0.48 | 16 | 1.41 | 16 |
| BS-HH-046 | 0.32 | 15.21 | 0.5 | 7.84 |
| BS-HH-050 | 0.12 | 16 | 0.13 | 0.35 |
| BS-HH-051 | 1.3 | >16 | 7.26 | >16 |
| BS-HH-054 | 0.11 | 16 | 0.17 | 0.43 |
| BS-HH-055 | 1.58 | 8 | 4 | 10.64 |

Example 3

Evaluation of the Aminated Homoharringtonine Derivatives of the Present Invention for Their Anti-Human Multiple Myeloma and Lymphoma Cell Activities (1) Experimental Materials Multiple myeloma and lymphoma cell lines: RPMI8226 (multiple myeloma), purchased from Fuxiang Bio-tech Co. Ltd., Shanghai, China.

Reagents: the same as in Example 2.

Main apparatuses: a Thermo Scientific 3111 incubator and a Bio-Rad iMark microplate reader.

(2) Experimental Method

Obtaining 6000 well-growing leukemia cells and inoculating them into wells of a 96-well cell culture plate. The culture medium is the 1640 cell culture medium containing 10% fetal bovine serum. After adding the homoharringtonine derivatives of different concentrations and mixing uniformly, placing the plate in a carbon dioxide cell incubator (5% $CO_2$) at 37° C. and incubating for 72 hours. Then the viable cell concentration is determined by the MTT method. In this experiment, the cell viability in control group (not treated with any compound) is set as 100%, and the cell viability (%) after treatment and the half maximal inhibitory concentration of the compound for the leukemia cell growth at 72 hours ($IC_{50}$ value of 72 hours) are calculated.

(3) The Experimental Results

The experimental results are shown in table 2. Table 2 shows that the aminated homoharringtonine derivatives of the present invention can induce the cell death of human myeloma and lymphoma cells and inhibit the growth of these tumor cells, wherein the aminated homoharringtonine derivatives, BS-HH-012, BS-HH-042 and BS-HH-054, of the present invention have demonstrated strong anti-RPMI8226 (multiple myeloma) effect.

Example 4

Evaluation of the Aminated Homoharringtonine Derivatives of the Present Invention for Their Anti-Human Solid Tumor Effect (1) Experimental Materials Human solid tumor cell lines: Hep-2 (human hepatocellular carcinoma), A549 (human lung cancer), CaES-17 (esophageal cancer cell), PC-3 (prostate cancer), CNE (nasopharyngeal carcinoma cell), and SK-OV-3 (ovarian cancer cell), all of which are purchased from China Center For Type Culture Collection; RKO (human colon adenocarcinoma cell), MGC 803 (human gastric cancer cell), MG63 (osteosarcoma) and U87 MG (malignant glioma cell), all of which are purchased from Fuxiang Bio-tech Co. Ltd., Shanghai, China; PANC-1 (pancreatic cancer), Huh7 (human liver cancer cell), Becap37 (human breast cancer cell), and Hela (human cervical cancer cell), all of which are donated by Cancer Research Institute of Zhejiang University, China.

Reagents: the same as in Example 2.

Main apparatuses: a Thermo Scientific 3111 incubator and a Bio-Rad iMark microplate reader.

(2) Experimental Method

Obtaining 4000 well-growing human solid tumor cells and inoculating them into wells of a 96-well cell culture plate. The culture medium is DMEM High Glucose cell culture medium containing 10% fetal bovine serum. The plate is placed in a carbon dioxide cell incubator (5% $CO_2$) at 37° C. and incubating for 24 hours. After adding the homoharringtonine derivatives of different concentration and mixing uniformly, the plate is placed in a carbon dioxide cell incubator (5% $CO_2$) at 37° C. and incubating for 72 hours. Then the viable cell concentration is determined by the MTT method and the cell viability (%) after drug treatment is calculated. In this experiment, the cell viability of control group (not treated with any compound) is set as 100%.

(3) The Experimental Results are Shown in Table 2.

Table 2 shows that the aminated homoharringtonine derivatives of the present invention can induce the cell death of human solid tumor cells and inhibit the growth of these tumor cells. The aminated homoharringtonine derivatives of the present invention BS-HH-012, BS-HH-042, BS-HH-046, BS-HH-050 and BS-HH-054, have demonstrated strong anti-A549 (human lung cancer), anti-PANC-1 (pancreatic cancer), anti-Becap37 (human breast cancer cell), anti-MG63 (osteosarcoma), anti-Huh7 (human liver cancer cell), anti-RKO (human colon adenocarcinoma cell), anti-Hela (human cervical cancer cell), anti-CaES-17 (esophageal cancer cell), anti-CNE (nasopharyngeal carcinoma cell), anti-Hep-2 (laryngeal carcinoma), anti-PC-3 (prostate cancer) and anti-SK-OV-3 (ovarian cancer cell) effect.

TABLE 2

Determination of the inhibiting concentrations of the aminated homoharringtonine derivatives on lymphoma, multiple myeloma and human solid tumor cell growth (72 h, $IC_{50}$ (µg/mL) value and $IC_{90}$ (µg/mL) value).

| | RPMI8226 | | A549 | | PANC-1 | | Becap37 | |
|---|---|---|---|---|---|---|---|---|
| Compound | $IC_{50}$ | $IC_{90}$ | $IC_{50}$ | $IC_{90}$ | $IC_{50}$ | $IC_{90}$ | $IC_{50}$ | $IC_{90}$ |
| HHT | 0.006 | 0.027 | 0.03 | >16 | 0.035 | >16 | 0.01 | 11.56 |
| BS-HH-008 | 10.97 | >16 | 16 | >16 | >16 | >16 | >16 | >16 |
| BS-HH-009 | 3.6 | 16 | 10.25 | >16 | 16 | >16 | 3.09 | >16 |
| BS-HH-011 | 6.71 | >16 | >16 | >16 | >16 | >16 | 11.32 | >16 |
| BS-HH-012 | 0.057 | 0.36 | 0.45 | >16 | 0.26 | >16 | 0.26 | 16 |
| BS-HH-014 | 2.43 | 16 | 9.79 | >16 | 8 | >16 | 6.89 | >16 |
| BS-HH-018 | 0.6 | 5.66 | 4.09 | >16 | 2.89 | >16 | 1.7 | >16 |
| BS-HH-020 | 16 | >16 | >16 | >16 | >16 | >16 | >16 | >16 |
| BS-HH-021 | 16 | >16 | >16 | >16 | >16 | >16 | >16 | >16 |
| BS-HH-025 | >16 | >16 | >16 | >16 | >16 | >16 | >16 | >16 |
| BS-HH-028 | 4.92 | >16 | 16 | >16 | 16 | >16 | 13.14 | >16 |
| BS-HH-034 | 0.47 | 3.72 | 1.74 | >16 | 1.94 | >16 | 0.81 | >16 |
| BS-HH-035 | 1.44 | 14.13 | 5.41 | >16 | 5.02 | >16 | 3.75 | >16 |
| BS-HH-037 | 1 | 9.86 | 1.96 | >16 | 6.47 | >16 | 1.5 | >16 |
| BS-HH-038 | 1.22 | 16 | 5.72 | >16 | 8.83 | >16 | 1.95 | >16 |
| BS-HH-041 | 1.96 | 13.36 | 8.11 | >16 | 6.35 | >16 | 0.9 | >16 |
| BS-HH-042 | 0.042 | 0.24 | 0.45 | >16 | 0.13 | >16 | 0.17 | >16 |
| BS-HH-043 | >16 | >16 | >16 | >16 | >16 | >16 | >16 | >16 |
| BS-HH-044 | 0.48 | 3.36 | 1.76 | >16 | 1.91 | >16 | 0.71 | >16 |
| BS-HH-046 | 0.17 | 0.72 | 0.84 | >16 | 0.45 | >16 | 0.4 | >16 |
| BS-HH-050 | 0.1 | 0.38 | 0.7 | >16 | 0.23 | >16 | 0.26 | 16 |
| BS-HH-051 | 1.7 | 16 | 6.96 | >16 | 6.84 | >16 | 1.99 | >16 |
| BS-HH-054 | 0.092 | 0.24 | 0.72 | >16 | 0.15 | >16 | 0.14 | 16 |
| BS-HH-055 | 2.1 | 16 | 11.21 | >16 | 8 | >16 | 5.9 | >16 |

| | MG 63 | | Huh7 | | RKO | | U87 MG | |
|---|---|---|---|---|---|---|---|---|
| Compound | $IC_{50}$ | $IC_{90}$ | $IC_{50}$ | $IC_{90}$ | $IC_{50}$ | $IC_{90}$ | $IC_{50}$ | $IC_{90}$ |
| HHT | 0.01 | 1.2 | 0.004 | 0.049 | 0.003 | 0.009 | 0.004 | 0.018 |
| BS-HH-008 | 15.5 | >16 | 11.22 | >16 | 4.44 | 16 | | |
| BS-HH-009 | 1.72 | >16 | 6.7 | >16 | 1.46 | 5.72 | | |
| BS-HH-011 | 6.33 | >16 | 16 | >16 | 4 | >16 | | |
| BS-HH-012 | 0.18 | >16 | 0.2 | >16 | 0.11 | 0.43 | 0.24 | 1.13 |
| BS-HH-014 | 6.24 | >16 | 4 | >16 | 1.25 | 5.36 | | |
| BS-HH-018 | 0.96 | >16 | 2.5 | >16 | 0.34 | 1.5 | | |
| BS-HH-020 | 14.14 | >16 | >16 | >16 | 8.38 | >16 | | |
| BS-HH-021 | >16 | >16 | >16 | >16 | 8.51 | >16 | | |
| BS-HH-025 | >16 | >16 | >16 | >16 | 15.35 | >16 | | |
| BS-HH-028 | 6.8 | >16 | 5.93 | >16 | | | | |
| BS-HH-034 | 0.32 | 16 | 1.05 | >16 | 0.18 | 1.25 | 0.89 | 5.74 |
| BS-HH-035 | 1.98 | >16 | 4.46 | >16 | | | | |
| BS-HH-037 | 1.44 | 16 | 16 | >16 | | | | |
| BS-HH-038 | 3.71 | >16 | 16 | >16 | | | | |
| BS-HH-041 | 1.97 | >16 | 16 | >16 | | | | |
| BS-HH-042 | 0.12 | 16 | 0.044 | >16 | 0.029 | 0.23 | 0.12 | 13.03 |
| BS-HH-043 | >16 | >16 | >16 | >16 | | | | |
| BS-HH-044 | 0.8 | >16 | 0.94 | >16 | 0.16 | 2.37 | 0.64 | 16 |
| BS-HH-046 | 0.23 | >16 | 1.37 | >16 | 0.054 | 0.93 | 0.25 | >16 |
| BS-HH-050 | 0.19 | 7.22 | 0.1 | 16 | 0.053 | 0.23 | 0.24 | 1.06 |
| BS-HH-051 | 2.72 | >16 | >16 | >16 | | | | |

TABLE 2-continued

Determination of the inhibiting concentrations of the aminated homoharringtonine derivatives on lymphoma, multiple myeloma and human solid tumor cell growth (72 h, $IC_{50}$ (µg/mL) value and $IC_{90}$ (µg/mL) value).

| | | | | | | | | |
|---|---|---|---|---|---|---|---|---|
| BS-HH-054 | 0.12 | 8.07 | 0.12 | 16 | 2.75 | 6.97 | 0.32 | 16 |
| BS-HH-055 | 3.83 | 16 | 4.83 | >16 | 2.75 | 6.97 | 6.54 | >16 |

| | Hela | | CaES-17 | | CNE | | Hep2 | |
|---|---|---|---|---|---|---|---|---|
| Compound | $IC_{50}$ | $IC_{90}$ | $IC_{50}$ | $IC_{90}$ | $IC_{50}$ | $IC_{90}$ | $IC_{50}$ | $IC_{90}$ |
| HHT | 0.019 | 16 | 0.037 | >16 | 0.038 | >16 | 0.014 | >16 |
| BS-HH-012 | 0.35 | >16 | 0.43 | >16 | 0.13 | >16 | 0.15 | >16 |
| BS-HH-034 | 1.97 | >16 | 1.91 | 16 | 0.49 | 16 | 1.29 | >16 |
| BS-HH-042 | 0.45 | >16 | 0.29 | 16 | 0.13 | >16 | 0.97 | >16 |
| BS-HH-044 | 1.91 | >16 | 1.63 | 16 | 0.76 | >16 | 1.23 | >16 |
| BS-HH-046 | 1.56 | >16 | 0.98 | 16 | 0.3 | 16 | 0.27 | >16 |
| BS-HH-050 | 0.46 | >16 | 0.46 | 16 | 0.15 | >16 | 0.31 | >16 |
| BS-HH-054 | 0.3 | >16 | 1.37 | >16 | 0.15 | 16 | 0.23 | >16 |

| | MGC 803 | | PC-3 | | SK-OV-3 | |
|---|---|---|---|---|---|---|
| Compound | $IC_{50}$ | $IC_{90}$ | $IC_{50}$ | $IC_{90}$ | $IC_{50}$ | $IC_{90}$ |
| HHT | 0.016 | 0.2 | 0.004 | 0.049 | 0.003 | 0.009 |
| BS-HH-012 | 0.24 | 6.84 | 0.32 | >16 | 0.41 | >16 |
| BS-HH-014 | 2.92 | 15.5 | | | | |
| BS-HH-018 | 0.94 | 4.96 | | | | |
| BS-HH-020 | 7.5 | >16 | | | | |
| BS-HH-021 | >16 | >16 | | | | |
| BS-HH-025 | >16 | >16 | | | | |
| BS-HH-028 | 8.62 | 24.34 | | | | |
| BS-HH-034 | 0.81 | 11.81 | 0.91 | >16 | 2.81 | >16 |
| BS-HH-035 | 1.79 | 9.2 | | | | |
| BS-HH-037 | 0.9 | 9.29 | | | | |
| BS-HH-041 | 1 | 11.84 | | | | |
| BS-HH-042 | 0.096 | 0.25 | 0.31 | >16 | 0.21 | >16 |
| BS-HH-043 | >16 | >16 | | | | |
| BS-HH-044 | 0.74 | >16 | 0.78 | >16 | 3.97 | >16 |
| BS-HH-046 | 0.39 | 8.28 | 0.78 | >16 | 1.89 | >16 |
| BS-HH-050 | 0.18 | 0.48 | 0.45 | >16 | 0.57 | >16 |
| BS-HH-051 | 1.9 | 26.73 | | | | |
| BS-HH-054 | 0.15 | 6 | 0.46 | >16 | 0.47 | >16 |
| BS-HH-055 | 6.06 | 18.97 | | | | |

The invention claimed is:

1. An aminated homoharringtonine derivative of formula (I)

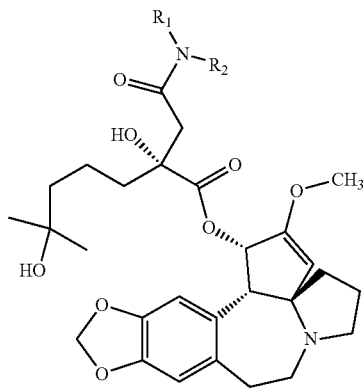

wherein
one of $R_1$ and $R_2$ is H and the other is independently selected from heteroaryl, heteroaryl-$C_1$-$C_4$ alkyl, wherein the heteroaryl is thiazolyl, furanyl or thienyl, or $R_1$ and $R_2$, together with the nitrogen atom to which they are attached, form N-heterocyclyl, aryl-N-heterocyclyl or heteroaryl-N-heterocyclyl, wherein the N-heterocyclyl is piperazinyl, morpholinyl, pyrrolidyl, thiomorpholinyl, pyrrolinyl, piperidyl, the aryl is phenyl, the heteroaryl is pyridinyl; wherein each of said groups is optionally substituted with one or more substituents selected from the group consisting of $C_1$-$C_4$ alkyl, halogen, $C_1$-$C_6$ alkyl amino, cyano, hydroxyl, and hydroxyl $C_1$-$C_6$ alkyl;
or a pharmaceutically acceptable salt thereof.

2. The homoharringtonine derivative or a pharmaceutically acceptable salt thereof according to claim 1, wherein one of $R_1$ and $R_2$ is H and the other is independently selected from heteroaryl, heteroaryl-$C_1$-$C_4$ alkyl, wherein the heteroaryl is thiazolyl, furanyl or thienyl, or $R_1$ and $R_2$, together with the nitrogen atom to which they are attached form N-heterocyclyl, aryl-N-heterocyclyl or heteroaryl-N-heterocyclyl, wherein the N-heterocyclyl is piperazinyl, morpholinyl, pyrrolidyl, thiomorpholinyl, pyrrolinyl, piperidyl, the aryl is phenyl, the heteroaryl is pyridinyl; wherein each of said groups is optionally substituted with one or more substituents selected from methyl, ethyl, isopropyl, hydroxymethyl, hydroxyethyl, hydroxyl, cyano, fluorine or chlorine.

3. The homoharringtonine derivative or a pharmaceutically acceptable salt thereof according to claim 1, wherein one of $R_1$ and $R_2$ is H and the other is furfuryl methyl or methyl furfuryl methyl, or $R_1$ and $R_2$, together with the nitrogen atom to which they are attached, form pyrrolidinyl, piperidyl, dimethylanimopiperidyl, 4-phenylpiperazin-1-yl or 4-(4-fluorophenyl)-piperazin-1-yl.
4. A homoharringtonine derivative or a pharmaceutically acceptable salt thereof, selected from the group consisting of
BS-HH-008
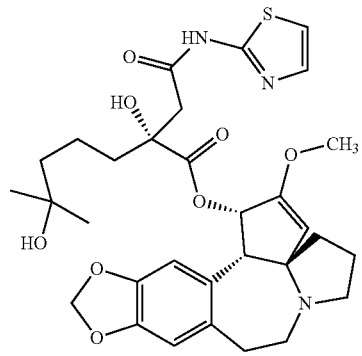
BS-HH-009
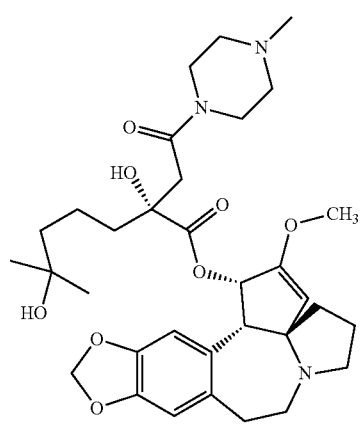
BS-HH-011
-continued
BS-HH-014
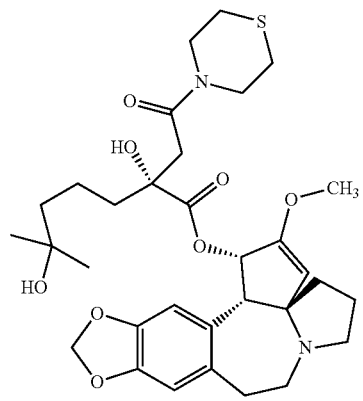
BS-HH-018
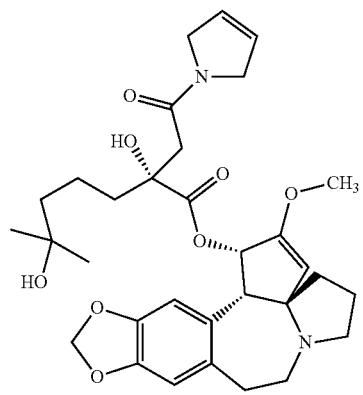
BS-HH-020
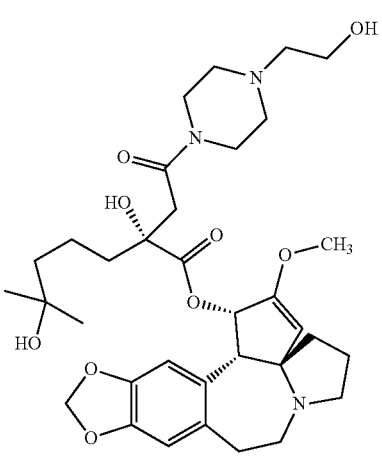

BS-HH-021
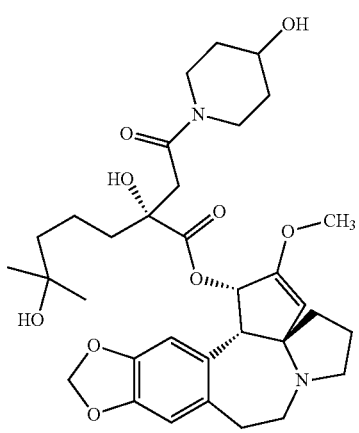
BS-HH-025
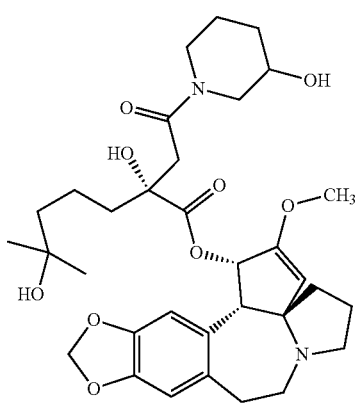
BS-HH-034
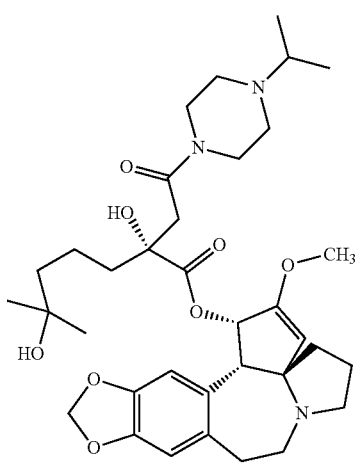
BS-HH-035
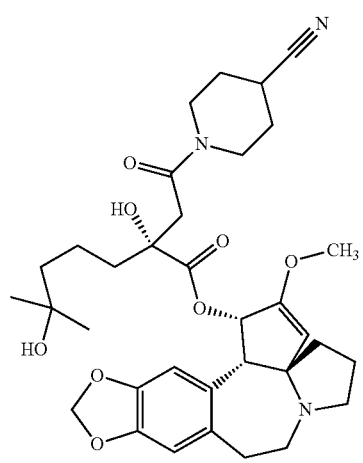
BS-HH-037
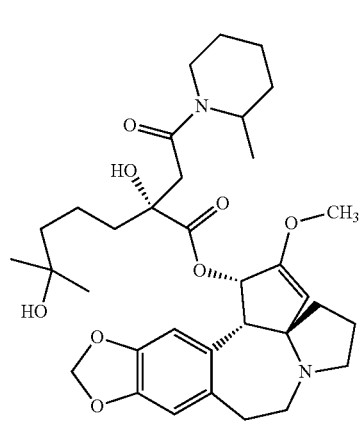
BS-HH-038
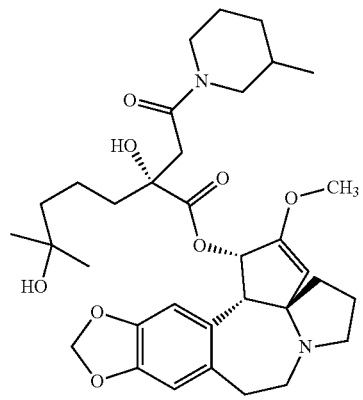

BS-HH-041
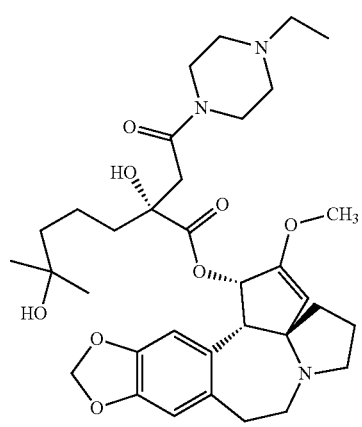
BS-HH-051
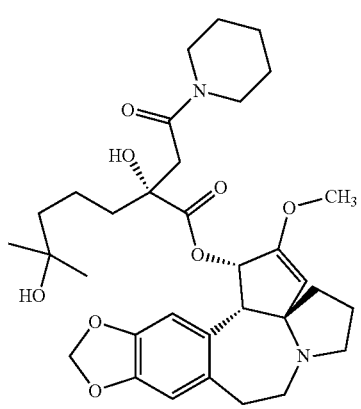
BS-HH-043
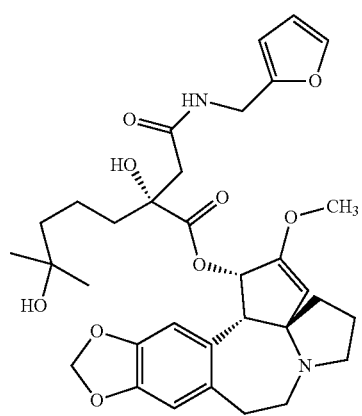
BS-HH-055
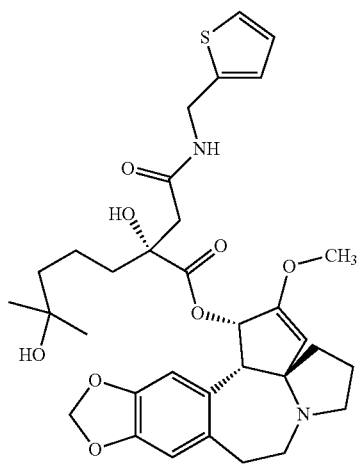
BS-HH-044
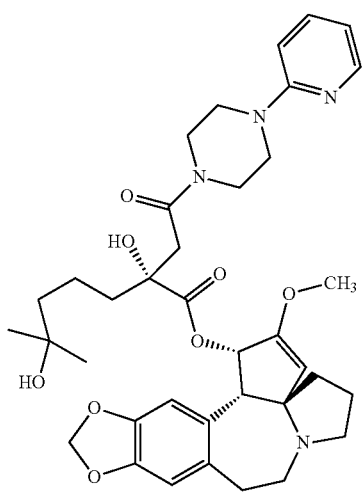
BS-HH-012
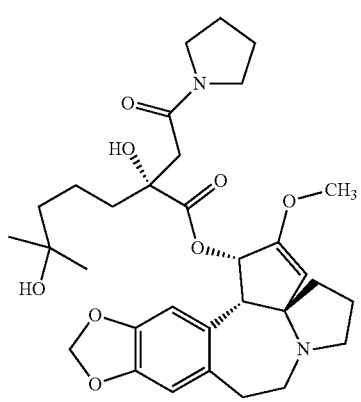

BS-HH-042

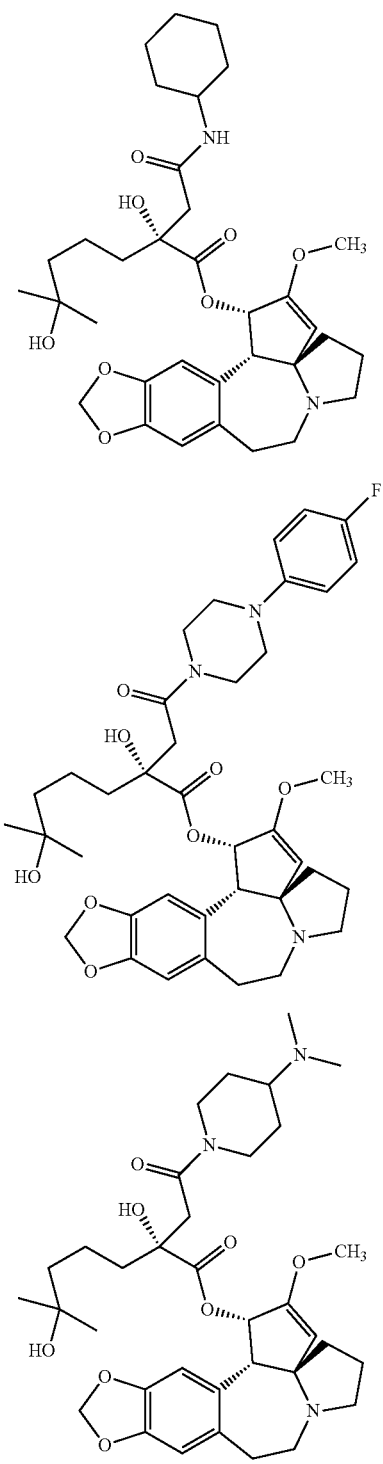

BS-HH-046

BS-HH-050

BS-HH-054

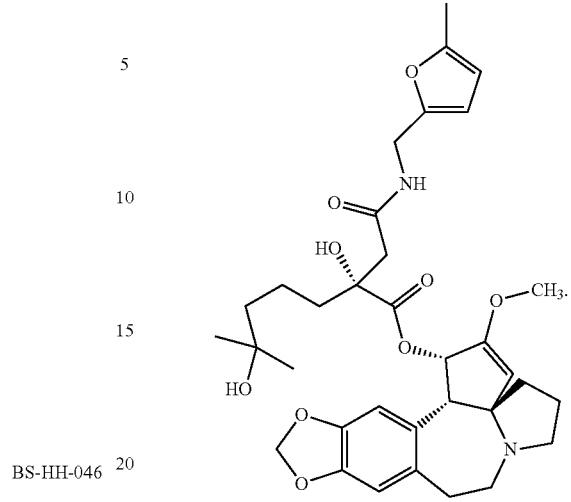

or a pharmaceutically acceptable salt thereof.

5. A pharmaceutical composition, comprising the aminated homoharringtonine derivative or a pharmaceutically acceptable salt thereof according to claim 1 and a pharmaceutically acceptable excipient.

6. A homoharringtonine derivative or a pharmaceutically acceptable salt thereof, wherein the homoharringtonine derivative is:

BS-HH-054

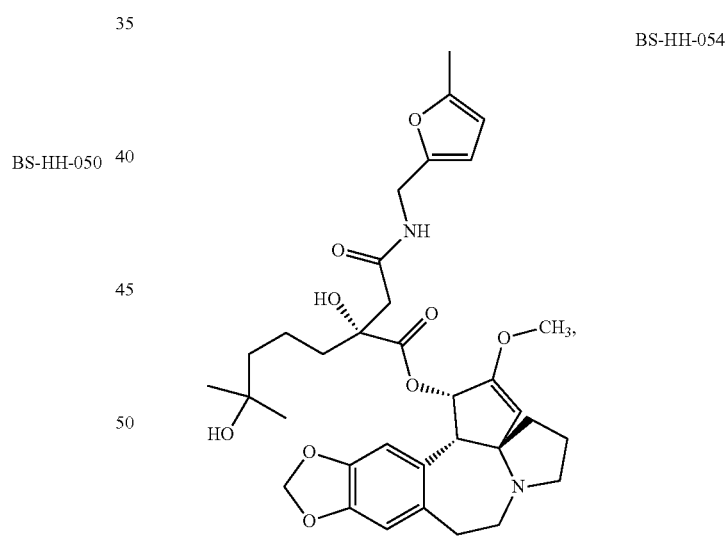

or a pharmaceutically acceptable salt thereof.

* * * * *